(12) United States Patent
Baarman et al.

(10) Patent No.: US 12,053,559 B2
(45) Date of Patent: Aug. 6, 2024

(54) DYNAMIC TREATMENT SYSTEM AND PATHOGEN REDUCTION DEVICES

(71) Applicant: UV Partners, Inc., Grand Haven, MI (US)

(72) Inventors: David W Baarman, Fennville, MI (US); Paul Byrne, Washington, DC (US); Colin J. Moore, Grand Rapids, MI (US); Hai D. Nguyen, Grand Rapids, MI (US); Luke Platz, Austin, TX (US); Ryan D. Schamper, Grand Haven, MI (US); Michael Halloran, Hudsonville, MI (US)

(73) Assignee: UV Partners, Inc., Grand Haven, MI (US)

( * ) Notice: Subject to any disclaimer, the term of this patent is extended or adjusted under 35 U.S.C. 154(b) by 435 days.

(21) Appl. No.: 17/364,189

(22) Filed: Jun. 30, 2021

(65) Prior Publication Data
US 2023/0001034 A1    Jan. 5, 2023

(51) Int. Cl.
A61L 2/24    (2006.01)
A61L 2/10    (2006.01)

(52) U.S. Cl.
CPC .................. *A61L 2/24* (2013.01); *A61L 2/10* (2013.01); *A61L 2202/11* (2013.01); *A61L 2202/14* (2013.01); *A61L 2202/25* (2013.01)

(58) Field of Classification Search
CPC .......... A61L 2/24; A61L 2/10; A61L 2202/11; A61L 2202/14; A61L 2202/25; A61L 2209/16; A61L 9/20
See application file for complete search history.

(56) References Cited

U.S. PATENT DOCUMENTS 10,413,624 B2 *   9/2019  Cole .................... A61N 5/0624
10,987,440 B1 *   4/2021  Sood ................... H05B 47/115
(Continued)

FOREIGN PATENT DOCUMENTS

WO    2018/039433    3/2018
WO    2019/190967    10/2019

OTHER PUBLICATIONS

International Search Report and the Written Opinion of the International Searching Authority for International Application No. PCT/US2022/033916 mailed Oct. 11, 2022.

*Primary Examiner* — David A Vanore
(74) *Attorney, Agent, or Firm* — Warner Norcross + Judd LLP

(57) ABSTRACT

A dynamic treatment system incorporates multiple pathogen reduction devices and sensors for enhanced pathogen reduction. The system can provide coordinated multi-level control to provide automated engineered control of pathogen reduction that is suitable for use in confined spaces, such as building and vehicle systems. Room level occupancy tracking provides biological load level estimates while pressure level sensing provides pathogen travel path estimation through the building. Combining this pathogen load information and airflow path information the system can drive room level and building level pathogen reduction device adjustments to enhance pathogen reduction based on expected pathogen travel. Zone level pathogen interception, height adjustable portable treatment devices, along with various application specific pathogen reduction devices can be integrated into the dynamic treatment system.

21 Claims, 23 Drawing Sheets

(56) References Cited

U.S. PATENT DOCUMENTS

| | | | |
|---|---|---|---|
| 11,184,739 B1* | 11/2021 | Wellig | H04W 4/029 |
| 2018/0330811 A1 | 11/2018 | Macary et al. | |
| 2019/0314535 A1* | 10/2019 | Golkowski | A61L 2/208 |
| 2020/0227159 A1* | 7/2020 | Boisvert | G08B 21/182 |
| 2022/0060856 A1 | 2/2022 | Wellig et al. | |
| 2022/0277851 A1* | 9/2022 | Wellig | F24F 11/30 |

* cited by examiner

DYNAMIC TREATMENT SYSTEM AND PATHOGEN REDUCTION DEVICES

BACKGROUND

The present invention relates to disinfection, and more particularly to systems and methods associated with disinfection.

It is well known that pathogens, i.e., bacteria, viruses, and other microorganisms, can cause disease or otherwise present significant health risks to human beings. A variety of efforts have been made to reduce risks associated with pathogens. For example, there is increasing interest in performing germicidal activities to reduce the number of pathogens in an environment. This is evidenced at least by the growing use of UV disinfection systems to perform repeated disinfection of a wide range of objects and environments.

There are currently quite a few different types of UV disinfection products available on the commercial market. However, many of these conventional UV disinfection products suffer from a variety of shortcomings that make them generally inefficient or ineffective at providing an engineered control solution for pathogen reduction. For example, many of these devices are not configured to communicate and respond to each other or to various sensor output in a systemic way. Instead, most UV disinfection products on the market are stand-alone solutions that cannot possibly hope to reduce the number of pathogens effectively and efficiently in a larger scale environment, e.g., a home or office building with multiple rooms, because among other deficiencies they lack the ability to collect, communicate, and act upon information to dynamically treat pathogen risks.

There has been dramatic growth in the use of networks to collect data relating to a range of activities in most environments, including homes, office buildings, passenger vehicle cabins, and medical environments. Although devices gather some data, e.g., data relating to temperature and occupancy, these and other data streams have not been effectively combined with treatment systems to understand their effect on pathogens let alone leveraged to reduce the overall pathogen level in an environment.

SUMMARY OF THE INVENTION

The present disclosure is generally directed to systems and methods for dynamically treating an environment with UV energy to reduce pathogens within the environment. Dynamic treatment systems and methods for pathogen reduction can be integrated with building management systems or compartment management systems. Several aspects of the present disclosure are directed to automated engineered control systems and methods for pathogen reduction that are suitable for use in confined spaces, such as building and vehicle systems.

Some aspects of the present disclosure relate to providing a coordinated multi-level pathogen mitigation system and interface. For example, device-level control can be supplemented with a local or room level control system. Activities of the pathogen reduction devices and information available to the devices can be coordinated and shared among the local devices to provide coordinated pathogen reduction within a local zone, such as a room of a building. This can include providing room level awareness of people, particulates, and biological loading, with the ability to adjust the performance level of the pathogen reduction devices individually or as a local group to dynamically compensate for pathogen loading within that zone/room. A global control system, which can include building level, floor level, or multi-room level control systems, can coordinate local sensor data to inform floor/building/multi-room level interactions that enhance pathogen mitigation. This can include adjustments in view of expected pathogen changes due to adjacent rooms, commons areas, portable units, restrooms, etc. Performance profiles or protocols can be driven by specific sequence and sensor thresholds. Various systems interactions and command sequences can be initiated by the system responsively to various criteria. For example, commands to surface treatment or other treatment devices can be issued responsively to information collected by the system at large. One specific example includes adjusting air sanitization level by commanding an HVAC system to alter air ducts, ceiling fans, or other components to impact temperature, humidity, and airflow within an environment. In this way, pathogens can not only be routed, but avoidance strategies can be implemented to direct pathogens away from high occupancy or overloaded areas, which can increase the overall effectiveness of pathogen reduction for an environment.

Another aspect of the present disclosure relates to setting and executing a cleaning response to a biological loading level. For example, a dynamic treatment system in accordance with the present disclosure can adapt unit interactions and/or average cleaning cycle completion percentages as factors in determining biological load per location. In general, the system can be configured to monitor interactions, which occur with human presence. By monitoring interaction levels for spikes in activity, the system can identify areas of pathogen loading, without the use of additional hardware sensors. Another consideration of the cleaning response involves associating components of the system. This can include a cloud-based configuration, with settings pushed to all devices located nearby the loaded area and devices further away receiving less-drastic setting changes. The "nearby" designation can be ascertained in a variety of different ways, including GPS capabilities, reception of audio from a smart speaker. In other configurations, the cleaning response can be executed without an Internet connection and instead via a device-based with a BLE mesh network and self-locating units that broadcast 'load levels' that other devices nearby are configured to react to. Devices that know about high loading can broadcast that information, and as devices that receive the information are further and further away from the broadcast source, they can be configured to react less drastically to the loading.

The dynamic treatment system can be configured to provide zone level pathogen interception. That is, the system can be configured to intercept or limit pathogens from migrating past a certain physical point breaking the potential chain of infection. The dynamic treatment system can be configured to operate as a coordinated swarm of pathogen mitigation devices.

The various components of the dynamic treatment system can form a data collection and agglomeration system of pathogen mitigation devices. The Amazon web services cloud infrastructure, artificial intelligence software, and medical diagnostic machine learning are just a few examples of components that can leverage the data collection and agglomeration system provided by pathogen mitigation devices. The data from the data collection/agglomeration sub system of a dynamic treatment system can collect and relay information regarding pathogen loading and building safety that can be used not only for pathogen reduction efforts but to build a larger overall picture useful in other disciplines as well. People counting, particle counting by zone, overall people and particulate counts, plume tracking by zone, are just some of the data pockets that can be collected and leveraged not only to effectuate pathogen reduction but also to present meaningful and significant visuals to users about the risk level and associated visualization of the global pathogen and other sensor values/data that moves and flows about the global environment of the system. This data can be used to configure the system to track plumes and people, which can be used not only in creating powerful visualizations, but also can be used to create mitigation strategies and response profiles (e.g., device/local/global pathogen reduction protocols) not only for that building environment, but for dynamic treatment systems in general. A response profile can include timing, performance levels and sequences of events that relate to desired and healthy outcomes.

Another aspect of the present disclosure relates to humidity sensing and temperature rise monitoring. One aspect of body generated pathogens is that initially body heat assists in the transfer or movement of such particles. The natural local humidity can be monitored with humidity and temperature sensors. Automotive, train, and plane cabins include sensors that can detect humidity locally as a product of breath. For example, in a vehicle, local seating positions can be monitored, and treatment can be administered in a load specific fashion.

Another aspect of the present disclosure relates to HVAC pre and post pathogen reduction mitigation. In homes and areas when HVAC changes or cycles the system can detect post cycle or change mitigation measures. The response profile in these cases may be both air treatment rates and surface treatment after some measured settling time. The settling time can be related to air flow and turbulence in that space.

Plasma treatment zones can be setup. Non thermal plasma may be part of the mitigation for pathogen reduction. Using a packed bed to deactivate pathogens allows a reliable method to treat specific use cases. UV and non-thermal plasma may be used to transform pathogens and chemicals for healthier outcomes. For example, a disinfecting fogger machine can be integrated into the dynamic treatment system as one of the pathogen reduction devices.

Another aspect of the present disclosure relates to an air curtain for a hospital bed. An air curtain hospital bed can have a battery powered and wirelessly charged air treatment system that pulls air away from the patient. This protects both the patient and the health care staff. Not only in the room but also in the hallways and potentially even on gurneys in the ambulance. The air is drawn from a point within the breathing zone, treated and exited. It uses a filter and UV and/or non-thermal plasma to deactivate pathogens. The air curtain can be incorporated into the bed rails or a structure about the patient's head and breathing zone and can be integrated into an overall dynamic treatment system as one of the controllable pathogen reduction devices that can have a device/local/global level.

Another aspect of the present disclosure relates to portable air treatment units with configurable heights for breathing zone variations. The portable units have multiple performance levels that can influence a wide change in pathogen load. The devices can accommodate multiple breathing zones in height. The device can be configured as an oscillating air treatment unit that can clean the surrounding area where a person is seated. Further, the portable air treatment units can be configured as pathogen reduction devices in a dynamic treatment system.

Yet another aspect of the present disclosure relates to passenger vehicle pathogen mitigation (e.g., airplane and train pathogen mitigation). Most airplanes and some trains have air vents associated with passenger seating. These vents have the opposite flow from your breath and the plume you breath. That is, these vents essentially take the air that is floating upward and scatter it downward and around the vehicle cabin. Instead, in this aspect of the present disclosure, these vents are reconfigured to instead intake passenger air upward and treat it using an air treatment system before returning that air back to the cabin. The same methodology and logic are also applicable in an automobile or train cabin environment.

Another aspect of the present disclosure relates to touch tracking. Touch interactions are generally indicative of human activity because they occur when people are physically present within an environment and interact with a surface being tracked by a touch sensor. Monitoring sensors for touch interactions and spikes in this activity enables a dynamic treatment system to identify pathogen/biological loading levels. That is, because there is a general correlation between the number of touch interactions in an area over time and the biological loading of a surface or group of surfaces, spikes in touch interactions are generally indicative of and a reasonable estimate of pathogen loading levels. Accordingly, touch interactions tracked by a system can be leveraged by a dynamic treatment system to execute adjustments based on pathogen loading level estimated by touch interactions.

Another aspect of the present disclosure relates to elevator pathogen mitigation. One embodiment relates to elevator airflow in segmented laminar sections. By creating segmented laminar airflow sections that do not easily mix an air curtain like effect between elevator passengers can be generated that is much more appealing than plexiglass or other physical barrier solutions. Air treatment, e.g., to recycle or expel air, can be built into the airflow system. Further, the elevator pathogen mitigation system can be integrated as part of a dynamic treatment system.

In general, the various devices and systems of the embodiments of the dynamic treatment system leverage strong correlations that exist between people and pathogens within an environment. To this point, the larger the number of people in an environment, the more likely a dangerous pathogen is to exist. Further, the dynamic treatment system can leverage existing systems and build upon the data provided by such systems to provide more effective and efficient pathogen reduction. For example, many modern buildings have occupancy sensing, on-demand-based lighting, or other building automation systems that can act as a stand-in for occupancy sensing. The dynamic treatment systems of the present disclosure can piggyback off these types of systems (as well as integrate other systems, not so routinely found in modern buildings) to collect information that can be utilized in pathogen reduction protocols and also to better understand occupancy and its relation to pathogens.

The dynamic treatment system can provide a programming interface layer that is seamless from a customer vantage point. That is, the system can collect data from multiple disparate sources that each represent occupancy. The dynamic treatment system can normalize these various events to provide a much more robust occupancy evaluation, in addition to utilizing the various sensor data for other response protocols. As an example, the dynamic treatment system can utilize not only an onboard occupancy sensor, but also access building occupancy data (e.g., keycard data), UV treatment device motion data, BLE pings from phones, touch sensor data, or other data indicative of occupancy, which can all inform occupancy as various event data to drive reactions or outcomes of the dynamic treatment system at a device, local (area), or global (building) level.

These and other objects, advantages, and features of the disclosure will be more fully understood and appreciated by reference to the description of the current embodiment and the drawings.

Before the embodiments of the disclosure are explained in detail, it is to be understood that the disclosure is not limited to the details of operation or to the details of construction and the arrangement of the components set forth in the following description or illustrated in the drawings. The disclosure may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the disclosure to any specific order or number of components. Nor should the use of enumeration be construed as excluding from the scope of the disclosure any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

DESCRIPTION OF THE CURRENT EMBODIMENTS

Figure 1:
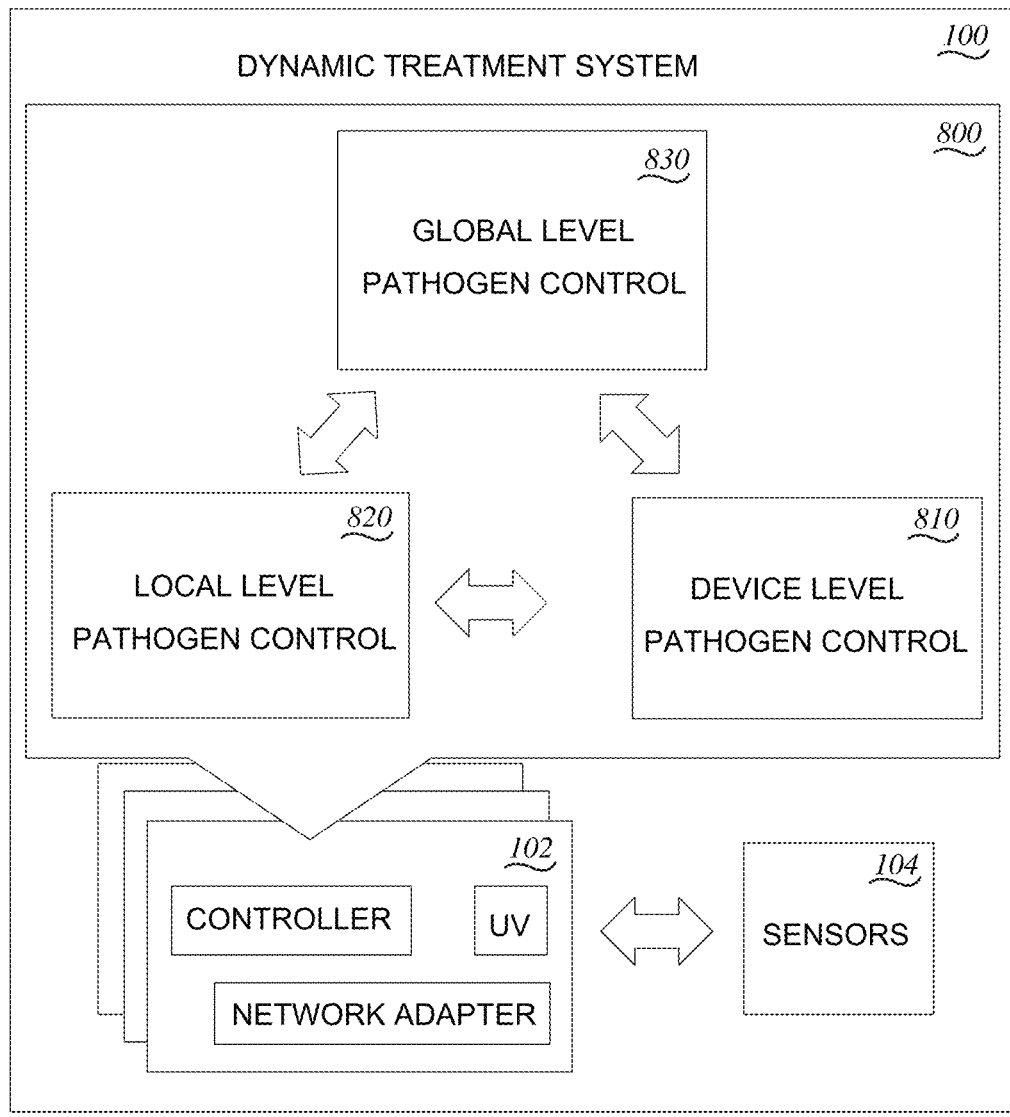
FIG. 1 illustrates a functional block diagram of a dynamic treatment system according to one embodiment of the present disclosure.

The present disclosure describes various embodiments and aspects of a dynamic treatment system. An exemplary dynamic treatment system 100 is illustrated in FIG. 1. The dynamic treatment system 100 includes multiple pathogen reduction devices that have coordinated operation to reduce pathogens or otherwise improve performance of the dynamic treatment system in an environment relative to pathogen reduction or performance without such coordination. The pathogen reduction devices 102 of the dynamic treatment system 100 can be configured to work in conjunction to dynamically treat an environment based on feedback from various sensors 104. Various embodiments and aspects of several exemplary pathogen reduction devices are described herein that may or may not be integrated into a dynamic treatment system. For example, air and surface pathogen reduction devices, portable and fixture-based pathogen reduction devices, breathing area pathogen reduction devices, and application specific pathogen reduction devices, to name a few different types of pathogen reduction devices, which are discussed herein.

Overview of Dynamic Treatment Systems and Methods.

FIG. 1 illustrates a functional block diagram of an exemplary dynamic treatment system 100 implemented in a building environment. The dynamic treatment system 100 coordinates control of multiple pathogen reduction devices 102 located in different rooms throughout the building based on a dynamic multi-level control method 800 and feedback from various sensors 104 located throughout the building as well as the pathogen reduction devices 102 themselves.

As discussed in more detail below, one aspect of the present disclosure is directed to systems and methods that implement a multi-level control methodology 800 that leverages device level control 810, local level control 820 (e.g., room level), and global level control 830 (e.g., building level). Feedback from the various devices within the system (e.g., pathogen reduction devices 102 and sensors 104) can be utilized to dynamically adjust operation of the pathogen reduction devices 102 to improve the overall effectiveness of the pathogen reduction.

In one aspect, to accomplish this coordinated pathogen reduction, each pathogen reduction device is configured with programming (e.g., stored in local memory) to operate according to a pathogen reduction protocol, which can be updated via a network connection. Baseline operation can be driven by a device level pathogen reduction protocol that is enforced at the device level, without influence from external devices during operation. A local level pathogen reduction protocol 820 can override the device level pathogen reduction protocol 810. Likewise, a global pathogen reduction protocol 830 can override the device level pathogen reduction protocol 810 and the local level pathogen reduction protocol, if present. These pathogen reduction protocols can be defined by a set of triggers and responses to those triggers, and therefore can be referred to respectively as global, local, and device response protocols.

Various embodiments and aspects of pathogen reduction devices, applications, and environments are described herein. The pathogen reduction devices can be implemented within a dynamic treatment system 100 according to an embodiment of the present disclosure. Some aspects relate to configurations of individual pathogen reduction devices and associated sensors, while other aspects relate to configurations of pathogen reduction devices and sensors collectively. Some aspects relate to obtaining or leveraging relative positions of pathogen reduction devices and controlling operation of the devices over time based on occupancy and other sensor data. Some aspects relate to identifying and responding to body generated pathogens. Body heat can play a significant role in the movement of such particles, especially within a confined space. Various systems and methods in accordance with the present disclosure can detect and/or respond to humidity and/or temperature levels indicative of a significant level or change in level of body generated pathogen particles. Further, some aspects relate to coordinating pathogen reduction devices based on specific information, such as schedule information, occupancy data, people counting sensors, light level sensors, particulate loading, and various other suitable trigger conditions or any other suitable trigger conditions.

Figure 3:
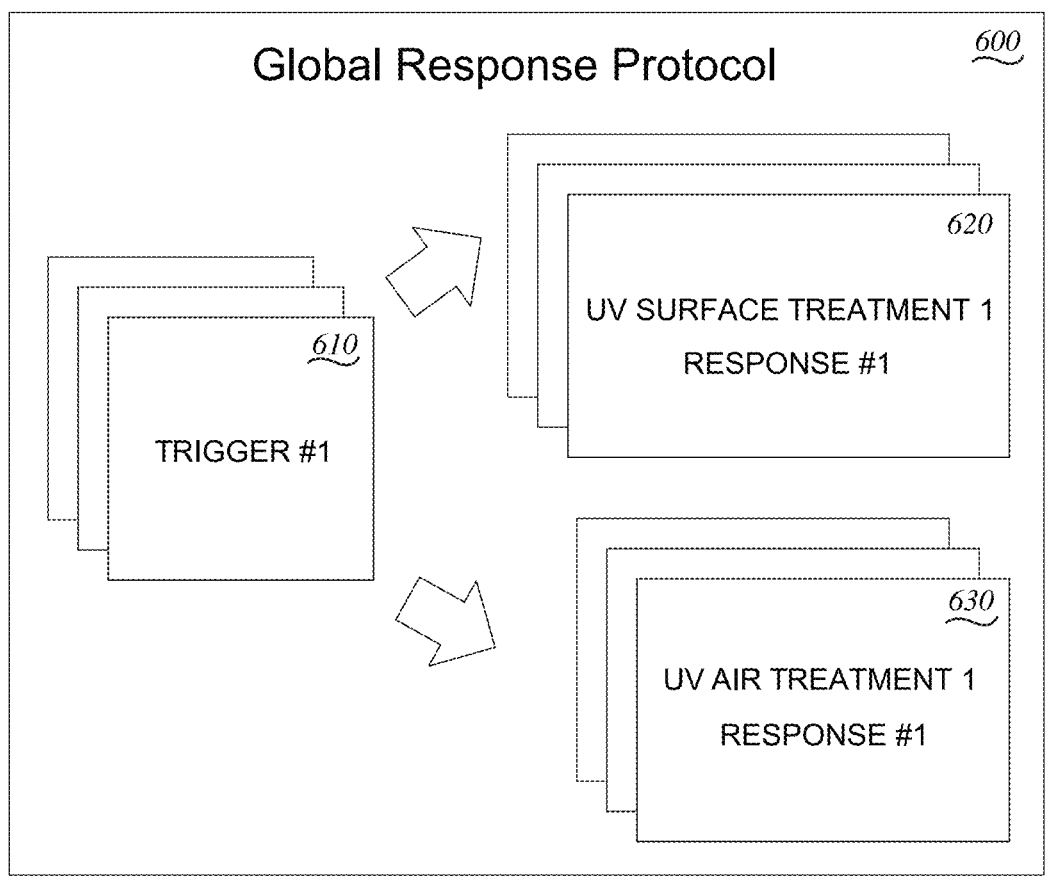
FIG. 3 illustrates a functional block diagram of multi-layer dynamic treatment for pathogen reduction according to one embodiment that integrates multiple surface and air treatment devices.

Response Protocols. A representative block diagram illustrating one exemplary embodiment of a global level pathogen reduction protocol 600 is shown in FIG. 3. The protocol defines an exemplary set of responses to various triggers, i.e., trigger criteria, and may be referred to as a global or building response protocol 600.

The building response protocol 600 can have several triggers 610 and each may have a defined set of responses 620, 630. The triggers 610 and the responses 620, 630 can have a compound structure that includes multiple conditions. For example, in response to a trigger 610 a controller implementing the building response protocol 600 may command a particular surface treatment device 620 and a particular air treatment device 630 to initiate a UV pathogen reduction cycle with a particular set of parameters. The responses 620, 630 can be tailored based on a variety of different factors. For example, one response 620 to certain trigger criteria may be provided for a particular type of pathogen reduction device (e.g., UV Surface Treatment devices) and a different response 630 to the same trigger criteria may be provided for a different type of pathogen reduction device (e.g., UV Air Treatment devices). In other examples, the responses may be based on other factors, such as the location of the UV treatment devices instead of or in addition to the device type.

In general, commands directed from the global response protocol override lower priority pathogen reduction protocols. Accordingly, even if the particular surface treatment or air treatment device would normally not initiate a cleaning cycle, because the global response protocol overrides the current protocol, the devices will begin their pathogen reduction. Alternatively, the parameters may not be a command to clean immediately, but rather perhaps to change the delay time (i.e., the amount of time the device waits after detecting presence before initiating a pathogen reduction cycle) or another pathogen reduction device setting. In this way, the global controller can implement global policies to provide more effective pathogen reduction based on information unavailable to the individual devices being commanded. In this scenario, the trigger may be a particular occupancy threshold being surpassed for the building and the command may be to shorten the delay time to counteract the expected increase in pathogen particles due to higher occupancy.

Another example of the global controller executing the response protocol 600 includes occupancy sensors and CO2 sensors tracking CO2 as a method to quantify occupancy and the volume of CO2 can be an indicator of a sum of the people in the room. As the warm air rises it make this measurement more accurate. Humidity and sound levels may also be used to add resolution to the dataset for potential increase in data resolution. The occupancy trigger may be directly by occupancy sensors or by the CO2 sensor limits. An example of the response for this trigger is first measuring ambient noise in the room by turning off the fans and listening for a predetermined settling period. If the ambient noise is measured above the upper fan speeds contribution to ambient the system may then switch speed for better treatment of the room. Multiple thresholds may be used to mitigate the number of people (source contamination) in the room. This keeps the air treatment sound levels reasonable and proportionate to the room level source contaminates. The system also has a dwell time by number of occupants wherein the system knows to remain on for a period of time when requested to shut down. This can be overridden but is used to conserve power. Not only the variable speed solution saves power but the knowledge of treating the source contaminates to a known level allows the system to turn off when occupancy is reduces or vacant. Additional triggers are used in this power reduction mode like pressure, especially high to low pressure transitions and HVAC awareness. If the pressure changes due to doors, elevators, HVAC or other reasons the response protocol is to cycle that room again as source contaminates are most likely moving in the related air transitions and then we monitor these conditions. Likewise, when the HVAC cycles this is also a source of contaminates and we cycle to remove the source contaminates from the room(s). Surfaces protocols may be activated and treated after some settling time to minimize on time and settled surfaces from being contaminated from the air particles settling. All programmable in a dynamic response protocol that can be refined as policy within workflow making the environment safer. It is designed to be tested and refined as the source contamination sources are measured and quantified with biological surveillance. This biological surveillance may be a real time input to the system and tracked as a reduction metric.

As another example, a global controller executing the global response protocol 600 can respond to the same trigger 610 by issuing a command to a particular UV surface treatment device 620. In this example, the response includes a command to wait for an amount of time (e.g., a delay time of about five minutes) after the trigger before communicating to the UV surface treatment device. In yet another example, an air treatment response 630 may include enabling a specific treatment protocol and performance level, for example a "medium" mode, which represents a set of parameters associated with a balance between UV cycle timings, UV intensity, and device availability, among other factors.

The global level controller can be configured to monitor whether the trigger conditions are met and administer the response(s) to facilitate execution of the global response protocol by communicating to the various pathogen reduction devices. In one embodiment, the triggers may be inputs to a cleaning or treatment system. Some example triggers can include particular thresholds or other values from monitored sensors, such as sensors that provide data indicative of people count (e.g. total people within the building, total people within a room, total people within a particular area), particulate levels (e.g. average level within the building, room levels, readings relative to historical data), humidity levels (e.g. output from a humidity sensor or multiple sensors, HVAC information indicative of humidity level, and various building statistics (e.g. room cleaning statistics, room usage statistics, conference usage statistics, restroom usage), and essentially any other global associated trigger. These are merely examples of advanced sensor readings that can be utilized in a dynamic treatment system in accordance with the present disclosure. The building level control system can engage a reactor (e.g., a pathogen reduction device) in response to essentially any given trigger.

One aspect of the present disclosure involves a data collection and agglomeration system for pathogen mitigation devices. Data from each dynamic treatment system regarding biological loading and building safety can be combined to build a larger overall picture. Biological loading generally refers to a measure of viable pathogens, number of people, number of pets, animals, plants, fungus, skin cells, or essentially any other biological. People counting, particle counting by zone, overall people and particulate counts, plume tracking by zone, creates a visualization of the global data that moves and flows. The data allows tracking of plumes and people for use in pathogen mitigation strategies and response profiles. A response profile can have timing information (e.g., UV lamp cycle time, UV intensity timing settings, delay timing), performance levels (e.g., control set points such as total UV exposure over a particular time period), and sequences of events that relate to improved health outcomes.

Many modern buildings have occupancy sensing and/or demand-based lighting (which can act as a form of occupancy sensing). The dynamic treatment system can be configured to interface with these, and other, systems to inform binary occupied/unoccupied space, as well as in some circumstances an occupancy count, such as that can be provided or deduced by information provided by WELL or LEED certified buildings.

The dynamic treatment system can include an application programming interface layer. The dynamic treatment system can be configured with various events that represent occupancy. The events can be collected and normalized at a server level. For example, the dynamic treatment system can combine onboard occupancy sensor data, building occupancy system data (e.g. occupancy sensors, motion sensors) received by the dynamic treatment system over a communication channel, workstation device occupancy data (e.g. computer sleep time and activity statistics, network traffic statistics, workstation occupancy sensors such as passive infrared sensors, BLE pings or other signals sourced from user smartphones detected by the dynamic treatment system, and other occupancy data available to the dynamic treatment system in one or more additional ways. These are just some examples of data that can trigger or contribute to a triggered event that drives a response (e.g., reaction or outcome) from the dynamic treatment system.

The trigger criteria and responses can be stored in memory. For example, the global controller can store the global response protocol including triggers and responses, the local controller can store the local response protocol including triggers and responses, and the device controllers can store the device response protocol including triggers and responses.

The relationship between trigger criteria (e.g., conditions) and the associated response(s) can form a trigger-pathogen reduction response event matrix that includes on one side, a list of monitored criteria, which, if met, cause the prescribed pathogen reduction reactions. In other words, essentially the relationship between trigger criteria and pathogen reduction responses is a pathogen reduction event matrix that tracks the relationship between a set of triggers and a set of responses (e.g., reactions). The triggers and responses may interact at a device, zone, or global level, depending on the application and configuration.

In some embodiments, the pathogen reduction triggers may act as pathogen reduction responses depending on the configuration and interactions. In one embodiment, the triggers are inputs to a pathogen reduction system. Some example triggers include occupancy; humidity; temperature; people counters; adapt motion and touch data; light switch usage; equipment movement/tracking system; equipment touch data; remote air quality sensors, device local and room local; meeting room scheduling system; and HVAC system. Specific illustrative examples of these examples are provided below.

By way of example, in embodiments where an HVAC system is utilized as a trigger, responses can include post response cleaning based on particle settling and mixing time. That is, some exemplary triggers involving an HVAC system can include direct and indirect triggers. Direct triggers refer to status and feedback directly provided by HVAC sensors or communication of status information. For example, a smart HVAC system can provide information about start, stop, runtime, fan speed, as well as other sensor data that the HVAC has access to. Indirect triggers refer to information about the HVAC system that can be inferred or deduced from other information. The indirect trigger information may be programmed into a dynamic treatment system or the dynamic treatment system can be programmed to detect HVAC system activity. For example, the dynamic treatment system may include a microphone or be connected to a device that has access to a microphone and the sound level or particular sound may be identified and associated with HVAC startup, HVAC shutdown, and other HVAC events. Then, these indirect associations can be utilized to trigger certain response in the dynamic treatment system without direct communication with the HVAC. The responses to HVAC events can be powerful for pathogen mitigation because air flow caused by an HVAC system can be an elusive source of pathogen distribution. By conducting some calibration methods, the dynamic treatment system responses can be tailored accordingly. For example, the air flow path when the HVAC is activated may always lead to pathogens traveling in one direction about a relatively fixed path in the building. Accordingly, by controlling intensity at certain spots along that path intelligently, the effectiveness of the pathogen reduction can be enhanced.

In one embodiment, the responses are outputs that react to certain selected dosage triggers. For example, in one embodiment, the pathogen reduction device can provide a variable speed and dosage. For example, U.S. application 62/956,816 to Baarman filed on Jan. 3, 2020, entitled SYSTEM AND METHOD OF DISINFECTION, which is hereby incorporated by reference in its entirety. In one embodiment, the reactor has variable dosage and timed events. For example, U.S. Pat. No. 9,242,018 to Cole filed on Oct. 2, 2013, entitled PORTABLE LIGHT FASTENING ASSEMBLY and U.S. Pat. No. 9,974,873 to Cole filed on Oct. 2, 2013, entitled UV GERMICIDAL SYSTEM, METHOD, AND DEVICE THEREOF, which are hereby incorporated by reference in their entirety. Another example reactor may be U.S. application 62/985,976 to Baarman filed on Mar. 6, 2020, entitled UV DISINFECTION PLATFORM, which is hereby incorporated by reference. In one embodiment, the response may be provided by a disinfection robot or mobile disinfection unit which may be deployed in response to a particular UV treatment trigger. In one embodiment, the response in the form of a command communicated to an HVAC system to control air exchange levels. For example, some HVAC systems can be remotely commanded and/or they can be controlled according to a set of parameters or set points.

Triggers can be based, at least in part, on touch tracking. That is, touch sensors can be available throughout the dynamic treatment system, such as at various workstations, reception areas, shareable devices, bathrooms, and various other locations, which can indicate touch activity. While touch activity can be utilized to inform a binary presence detection trigger, it can also be utilized for more advanced triggers. For example, because touch interactions generally occur in the presence of human beings, monitoring touch activity levels for spikes in activity can substitute for a measure of human loading that is more precise than a general motion sensor, without having to devote resources to new hardware specifically for people counting.

Multi-Level Pathogen Control. One aspect of the present disclosure is generally directed to dynamic treatment systems and methods that involve multiple coordinated pathogen reduction devices and sensors that work in conjunction. Perhaps as best shown in the exemplary block diagram of FIG. 1, a dynamic treatment system 100 can organize and leverage multiple different levels of pathogen control 800 to provide an overall more effective (e.g., larger amount of or more efficient) pathogen reduction relative to systems with standalone pathogen reduction devices.

The exemplary dynamic treatment system of the present disclosure is programmed as a three-tier pathogen reduction control structure 800: device level pathogen control 810, room level pathogen control 820, and building level pathogen control 830.

In general, device level pathogen control 810 refers to the control algorithm or set of algorithms stored in memory on each pathogen reduction device that, when executed, set a baseline default operation for each pathogen reduction device based on the functionality of that particular device. That is, in some embodiments, each pathogen reduction device 102 can be selectively configured to operate in isolation on its own without coordinating with other pathogen reduction devices 102 in the network 100. This level of pathogen control can be referred to as device control, isolated control, or another suitable name.

Device level control will be discussed within the context of several specific examples below, but suffice it to say, device level control generally refers to a standalone pathogen reduction mode, i.e., where the pathogen reduction device can operate without influence from other pathogen reduction devices. That is, a pathogen reduction device, such as an air treatment device or surface treatment device that includes a UV-C lamp that generates UV energy device, includes a controller, memory, a UV source, and often, but not always, has access to sensor data from a sensor associated with the device, e.g., a sensor included on the device connected to the controller or a sensor coupled via a wired or wireless communication connection. The pathogen reduction device controller is generally configured to execute a program stored in memory that controls various aspects of the UV source based on the sensor data of the device associated with the sensor. For example, the pathogen reduction device may be a workstation treatment system that activates and deactivates based on sensor data from a proximity sensor installed at the workstation that is configured to detect human presence or lack thereof. Such devices are described in a number of different patents and patent applications, including U.S. Pat. No. 10,413,624, filed Feb. 22, 2018, entitled PORTABLE LIGHT FASTENING ASSEMBLY and U.S. Appl. No. 62/985,976, filed Mar. 6, 2020, entitled UV DISINFECTION PLATFORM, which are each hereby incorporated by reference in their entirety. As another example, the pathogen reduction device may be an air treatment system. One example of such a device is described in U.S. Appl. No. 62/956,816, filed Jan. 3, 2020, entitled UV AIR TREATMENT, which is hereby incorporated by reference in its entirety.

In general, local level pathogen control 820 refers to the control algorithm or set of algorithms stored in memory associated with one or more local level pathogen reduction control devices within a particular zone that, when executed, cause the multiple pathogen reduction devices 102 located in the zone to operate in conjunction with each other. The zone can be defined as a room of a building, a particular area of a building, a proximity measurement between the devices, or essentially any other way of defining a zone. This local level of pathogen control can also be referred to as room level pathogen reduction control, zone level pathogen reduction control, or proximity level pathogen reduction control, or another suitable name.

Local level control 820 will be discussed in the context of several examples below, but generally it refers to multiple pathogen reduction devices situated in proximity of one another coordinating their operation to provide more effective pathogen reduction of a zone. That is, in general, local level pathogen control 820 refers to one or more algorithms that can be programmed on one or multiple controllers that enables communication between the devices, one-way or multi-way, such that at least one of the devices operates more effectively than it otherwise would without the local level pathogen control. Providing a more effective zonal pathogen reduction can refer to the overall amount of pathogen reduction per unit time, time efficiency—referring to how quickly the pathogen reduction is achieved, power efficiency—referring to how much energy was utilized to reduce the pathogens to a certain level. In some local level pathogen control schemes, the pathogen reduction devices communicate sensor information, and each device is configured to alter its operation based on the additional sensor information. In other local level pathogen control schemes, the pathogen reduction devices have a master/slave relationship where the slave pathogen reduction devices (including any associated sensors) can communicate information regarding their operation and sensor data to the master pathogen reduction device, which can be programmed to determine pathogen reduction device settings for some or all of the pathogen reduction devices according to a local pathogen reduction criterion. In some embodiments, a dedicated local controller that may or may not have pathogen reduction functionality can act as the master node and communicate with the local pathogen reduction devices.

In general, global level pathogen control 830 refers to the control algorithm or set of algorithms stored in memory associated with essentially any designated global controller or set of global controllers. The global controller can be a standalone local controller, one of the controllers of a pathogen reduction device 102 in the system, a remote cloud controller, or essentially any other designated controller within the dynamic treatment system 100. In some embodiments, the global controller functionality may be distributed among some or all of the other controllers in the dynamic treatment system, such as the various pathogen reduction devices 102. Even where a dedicated global controller is implemented, instructions (e.g., global, and local instructions) will generally be provided by the global controller to the pathogen reduction devices 102 in order to implement the multi-level pathogen reduction control method 800.

Global level control 830 will be discussed in the context of several examples below, but generally refers either to coordinating multiple (1) groups of pathogen reduction devices or (2) individual pathogen reduction devices, to provide more effective global pathogen reduction. Providing a more effective global pathogen reduction can refer to reducing the overall amount of pathogen reduction per unit time in total within the global space, pathogen reduction time efficiency (i.e., how quickly a global target pathogen reduction is achieved), power efficiency (i.e., how much energy is utilized to reduce the pathogens to a target global level), to name a few examples of criteria for effective global pathogen reduction. It is worth noting that the global pathogen reduction control is generally concerned with net results—that is, it may involve one or multiple zones being less efficient or having less pathogen reduction in order to achieve a higher overall efficiency or overall larger pathogen reduction. Global level pathogen control can also be referred to as building level pathogen reduction control, or another suitable name. Lamp or LED life can be enhanced by limiting lamp on time. Further, by utilizing the lamp on time more effectively, efficiency can be increased. For example, the lamp on time can be controlled intelligently with more efficiency directed to source contamination, that is, effectively configuring the system such that the lamp on time coincides with times where the source has a higher level of pathogen contamination. Such a treatment protocol can effectively leverage sensors to reduce energy usage, which in turn reduces maintenance costs and can be a large savings in energy usage over time, especially at scale.

Pathogen Reduction Devices. Various embodiments and aspects of several exemplary pathogen reduction devices are described herein that may or may not be integrated into embodiments of a dynamic treatment system. For example, air and surface pathogen reduction devices, portable and fixture-based pathogen reduction devices, breathing area pathogen reduction devices, and application specific pathogen reduction devices, to name a few different types of pathogen reduction devices discussed herein may be included in some, but not necessarily all, of the various dynamic treatment systems of the present disclosure.

The room or local level pathogen control 820 can include a monitoring component that can be configured through a variety of systems and methods. For example, monitoring can be performed through one or a combination of people counting devices, HVAC sensors, humidity level sensors, $CO_2$ level sensors, pressure sensors temperature sensors occupancy sensors, light sensors, air quality sensors, and touch sensors, to name a few different monitoring devices that can be configured to operate within the dynamic treatment system. This monitoring can be leveraged to dynamically adjust the pathogen reduction devices at a local level to reduce pathogens according to a local level pathogen protocol.

The global or building level pathogen control 830 can also include a monitoring component that can be configured through a variety of systems and methods, which can be leveraged to reduce pathogens in a building or global area according to a global pathogen reduction protocol or strategy. The building pathogen control 830 may have variable building level pathogen mitigation. For example, the pathogen mitigation techniques may vary based on sensor data provided to the system such as occupancy level (e.g., the global level pathogen control system can be configured to adjust the pathogen devices differently in response to a minimum or lower occupancy compared to a maximum or higher occupancy level). Similarly, other data spatial mappings (e.g., heat maps) of occupancy levels/people counts, pressure levels, air quality levels, temperature levels, humidity levels, or other pathogen level data factors can be leveraged to adjust pathogen devices. The building pathogen control 820 may have global sensing capabilities and may respond to a variety of inputs. For example, the global or building level pathogen control system 830 may respond to air quality sensing, temperature sensing, humidity sensing, occupancy sensing, pressure sensing, and maintenance feedback. The ability for the system (and users of the system) to have access to pressure levels on a room-by-room basis, e.g., such as the differences between pressure levels of connected rooms, the system can be configured to determine (and display or act upon) air flow vectors (i.e., direction and flow rate) as well as make determination about how connected spaces will be impacted by source contaminants. By way of example, FIG. 7 illustrates how the dynamic treatment system can be configured to react to sensed pressure levels and pressure level differentials. Specifically, FIG. 7 illustrates an exemplary response to the pressure levels sensed in FIG. 6. Because airflow generally moves from higher pressure areas (e.g., the general gathering space 590) to lower pressure areas (e.g., smaller rooms 592, 594), the system can be configured to increase dosage or treatment level for lower pressure level spaces adjacent to higher pressure level spaces due to the expectation of pathogens to move as indicated by the airflow arrows 560. The step up in treatment level in the adjacent rooms can be configured as a discrete change in treatment level (e.g., change in UV on-time, UV intensity, delay time, shutoff sensitivity (e.g., in response to motion or activity), or any of a plethora of other pathogen reduction device changes that can impact UV treatment level or dosage. The change in dosage or treatment level can be proportional or otherwise related to the pressure differential between the adjacent rooms. The change in dosage or treatment level can be proportional or otherwise related to contamination source information, such as humidity levels, people count information, or other information about the number of pathogens being introduced into the higher-pressure area. Further, the adjustments to the pathogen reduction devices in the adjacent, lower pressure, areas can be made relative to any local or device level adjustments being made based on the status of the room or device level protocols. For example, while the treatment level or dosage may be increased due to the pressure differential, it may be further adjusted due to additional people entering or leaving the space. There may be a maximum or minimum level of treatment or dosage level that can be driven by device or local level protocols, but the dynamic treatment system can still track the various inputs and events and track when a capped dosage situation arises, which can help to identify where further dosage maximums may be relevant and desired for this space or for future systems being designed to accommodate pressure differentials.

At the device level 810, the devices can monitor, and control pathogen level based on a variety of methods. For example, the device level 810 may perform variable mitigation based on minimum to maximum occupancy and may have local response protocols. At the device level 810, the fans on a dynamic air treatment system may be set to low, medium, or high, and the dosage may be set to low, medium, or high. The device level 810 may have local sensing and may respond to a variety of inputs. For example, the device level 810 may respond to air quality sensing, temperature sensing, humidity sensing, occupancy sensing, pressure sensing, and maintenance feedback.

The dynamic treatment system 100 can include a coordinated multi-level mitigation interface. The first level can include local control and room level performance. The second level can include room level awareness of people, particulates and biological loading, with the ability to change the performance level dynamically to compensate for room loading. The third level can be a global control system reading local sensor data to inform floor level and building level interactions that enhance mitigation. Adjacent rooms, commons areas, portable units, restrooms etc. Driving performance profiles for specific sequences and sensor thresholds. A fourth level may be included that emphasizes systems interactions and sequences. For example, coordinating interaction with an HVAC system, temperature, humidity, and/or surface treatment systems. Turn ON higher level of Air Sanitizing (example HVAC air duct, ceiling fan.)

Figure 2:
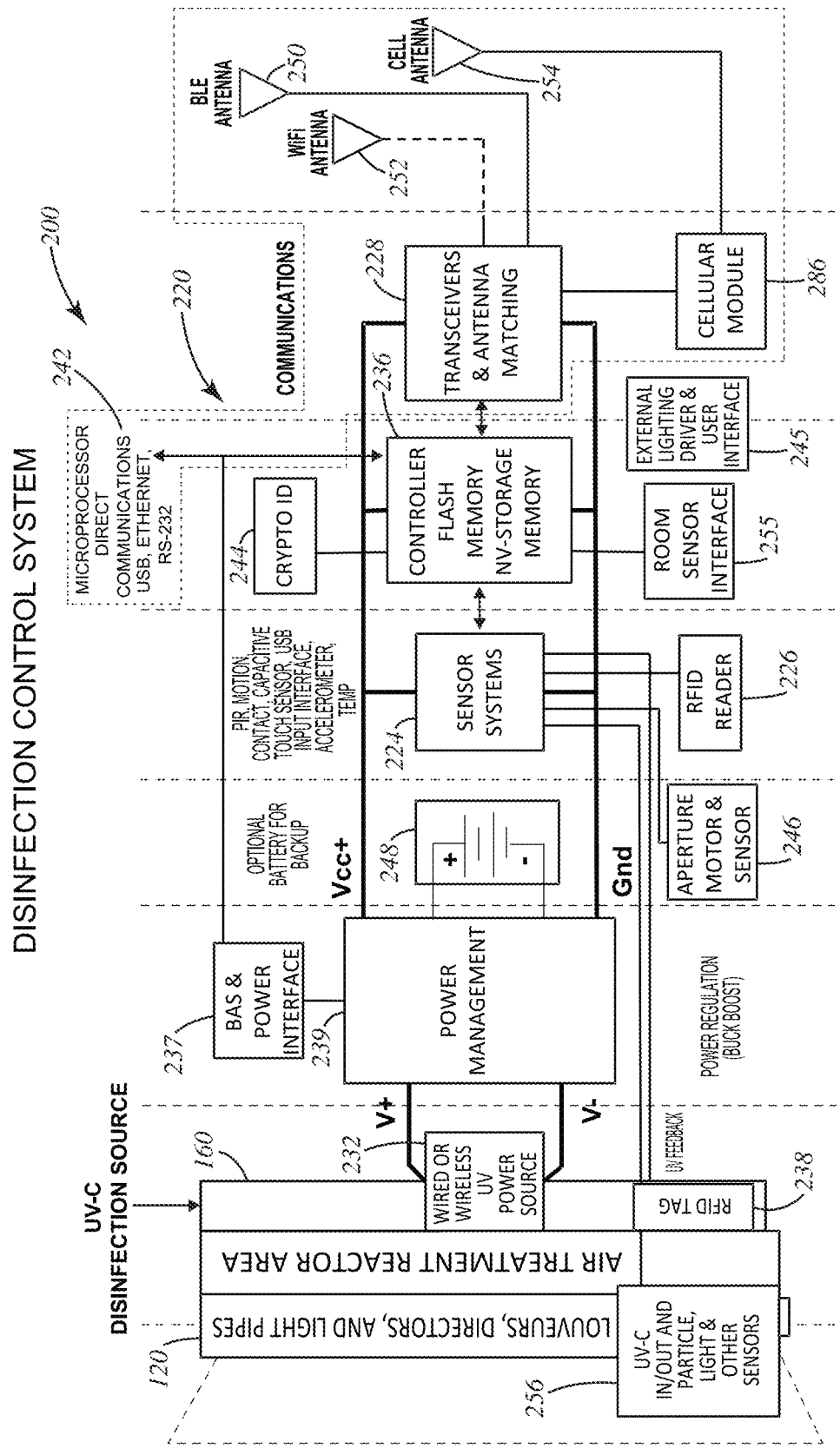
FIG. 2 illustrates a functional controller block diagram of a dynamic treatment system controller according to one embodiment of the present disclosure.

An exemplary pathogen reduction device will now be described in connection with the air treatment system of FIG. 2. In particular, the pathogen control system 200 of the illustrated embodiment controls operation of a UV light fixture 160 and components thereof. The control system 200 may be configured as an Internet-of Things ("IOT") hub or node within a network. The control system 200 in one embodiment may be operable to detect and identify the location for terminal cleaning equipment.

The control system 200 may include power management capabilities and an optional battery management system for safety and emergency purposes. One or more sensors may be provided to detect in-room conditions for relaying to the dynamic treatment system 100 as well as to help inform the device level response protocol. The system may include an industrial automation interface for control and energy management. The control system may include a UVC sensor to understand dose and time for the air reactor and the surface treatment. Power management may include one or more of the following operations: delayed off, intermittent cycle scheduling, dimming, power monitoring, and accounting, and on/off control.

The control system 200 in the illustrated embodiment includes a UV light power source 232 (e.g., a UV-C power source) that enables UV intensity control and contact time control. The UV light source 160 may be any UV source capable of generating UV light at the target intensities, including UV-C light at the target intensities. The UV light power source 232 may be capable of controlling current and/or voltage supplied to the UV light source 160 and may provide such power in a variety of ways. For instance, the UV light power source 232 may supply power directly via wires to the UV light source 160, or the UV light power source 232 may supply power wirelessly to the UV light source 160. In the wireless configuration, the UV light power source 232 may include a primary capable of transmitting power wirelessly, and the UV light source 160 may include a secondary capable of receiving the wirelessly transmitted power.

The control system 200 of this embodiment may include a controller 236 capable of performing various functions pertaining to operation of the light fixture. The controller can be a low current microprocessor configured on a regulated rail. The microprocessor can be configured to monitor temperature (e.g., ambient, source, and local microprocessor temperature), accelerometer values, voltage, and current sensors, as well as any other suitable sensors for use in conjunction with a microprocessor, or any combination thereof. The microprocessor module can also allow for external communications and interface.

In the illustrated embodiment, the controller 236 is coupled to a sensor system 224 that provides the control system 200 with various sensor inputs, such as PIR sensors, motion sensors, capacitive touch sensors, accelerometer and temperature sensors, and may provide an interface for RFID reader 226. The data collected by these sensors may assist in controlling operation of the control system 200 and in collecting data that may be relevant to tracking on infection-related events. The touch sensing aspect in accordance with one embodiment enables touch events to be used to trigger UV source activation, to interrupt disinfection cycles, and to provide valuable data in making dynamic adjustments to the UV parameters, such as cycle time and source intensity. The PIR sensor in one embodiment may enable heat and motion tracking. Additionally, or alternatively, capacitive touch sensing may enable tracking touches of grab handles and non-switch surfaces.

The sensor system 224 in one embodiment may include a particle sensor capable of sensing information about particles present in the air that is external or internal, or both, with respect to the treatment chamber 110. The control system 200 may vary operation at a device level based on the particle information obtained from the particle sensor and may also pass such information back to the dynamic treatment system for use in making adjustments at a local and/or global level.

In one embodiment, the control system 200 may be coupled to a cloud system also as described herein as a cloud-based control system 3602. The cloud system 3602 may obtain multiple particle sensor readings for an environment, and direct fan speeds and on times to treat a plume of particulates within a larger environment of multiple devices (e.g., multiple air pathogen reduction systems) in a connected pathogen reduction system.

The controller 236 in one embodiment may monitor the current and voltage of power supplied to the UV light source 160 and may determine whether the current and/or voltage are within preset ranges for proper operation and lamp diagnostics. UV light sources 160 can present open circuits, short circuits, or impedance changes causing different operating voltages. The controller 236 may identify such conditions based on the current and/or voltage and send information pertaining to such conditions to a remote network component, such as a network server on the cloud, as a service request. In one embodiment, the UV light power source 232 monitors the current and voltage to the UV light source 160 and feeds that information back to the controller 236. The controller 236 may also include volatile and and/or non-volatile storage memory. For example, the controller 236 may include flash memory.

In one embodiment, the UV light source 160 and control system 200 have integrated RFID capabilities. An RFID tag 238 disposed on the UV light source 160 may allow the controller 236 to uniquely identify the UV light source 160 using an RFID reader 226. This allows the control system 200 to properly validate the UV light source 160 and also allows new thresholds (e.g., operating currents and/or voltages and other operating parameters) to be transferred to the controller 236 for the particular UV light source 160 connected to the light fixture 100. These thresholds may change by manufacturer or lamp time and can also be changed over time as the controller 236 adapts and learns the operating parameters of the UV light source 160.

The UV light power source 232 in one embodiment includes an amplifier circuit, where an amplifier gain can be changed to increase or decrease intensity of the UV light source 160. The amplifier may change the voltage applied to the UV light power source 232 to within allowed thresholds. It is noted that higher thresholds or operating near the upper end of a voltage range of the UV light source 160 may adversely affect the life of the UV light source 160. The operating intensity thresholds, operating ranges, or other operating conditions for the UV light source 160 may also be pushed and saved to the RFID tag 238. For instance, the hours at each intensity level may be helpful to the controller 236 as it may accumulate the time at each intensity for the UV light source 160 to enable total end-of-life calculations. This information may be persistent to the RFID tag 238 of the UV light source 160 so that, if the UV light source 160 to another light fixture 100, that light fixture 100 can be aware of operating parameters and an end of life associated with the UV light source 160.

Figure 14:
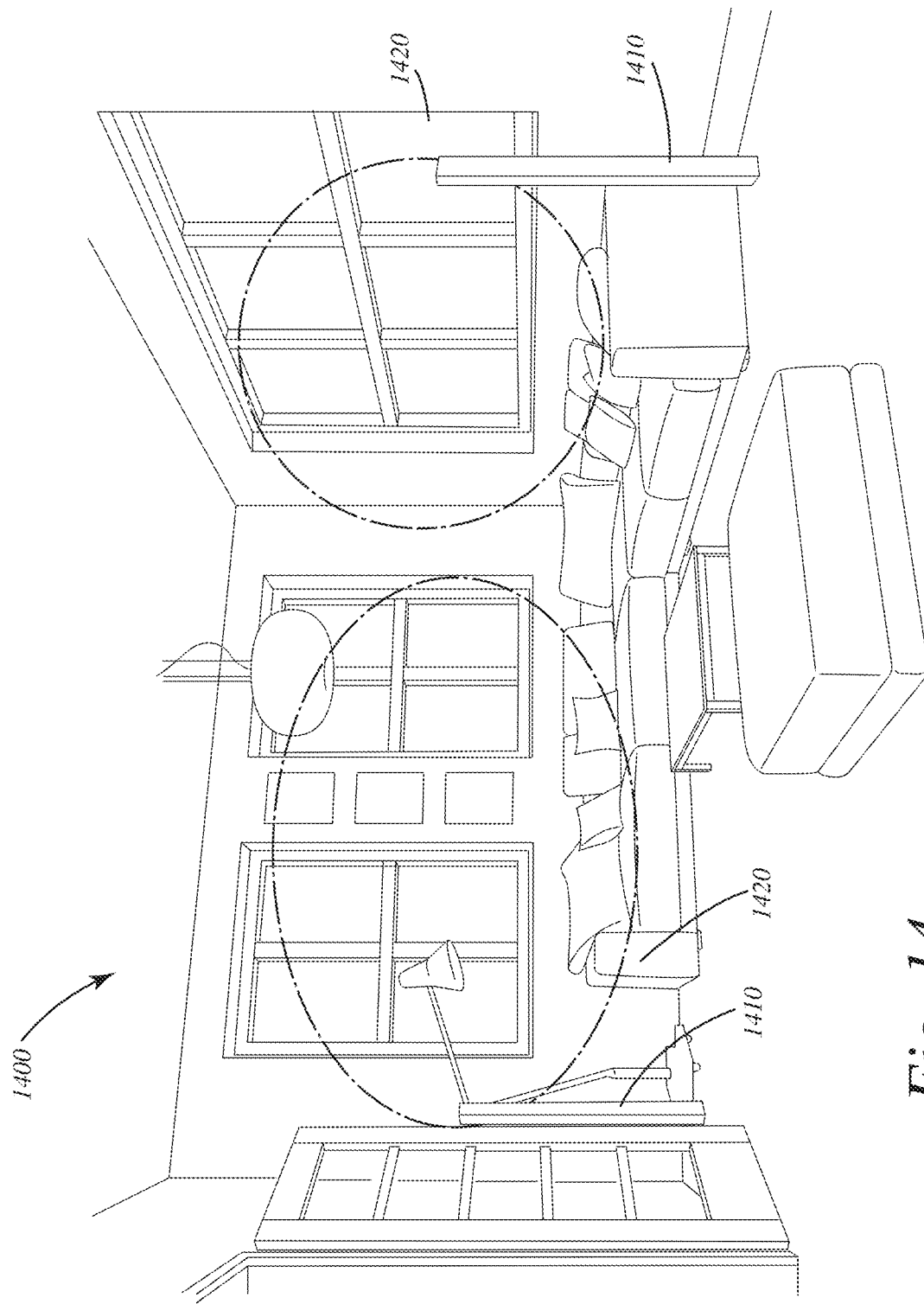
FIG. 14 shows an exemplary arrangement of portable pathogen reduction devices configured to cooperate as a dynamic air treatment system in a residential environment.
Figure 15:
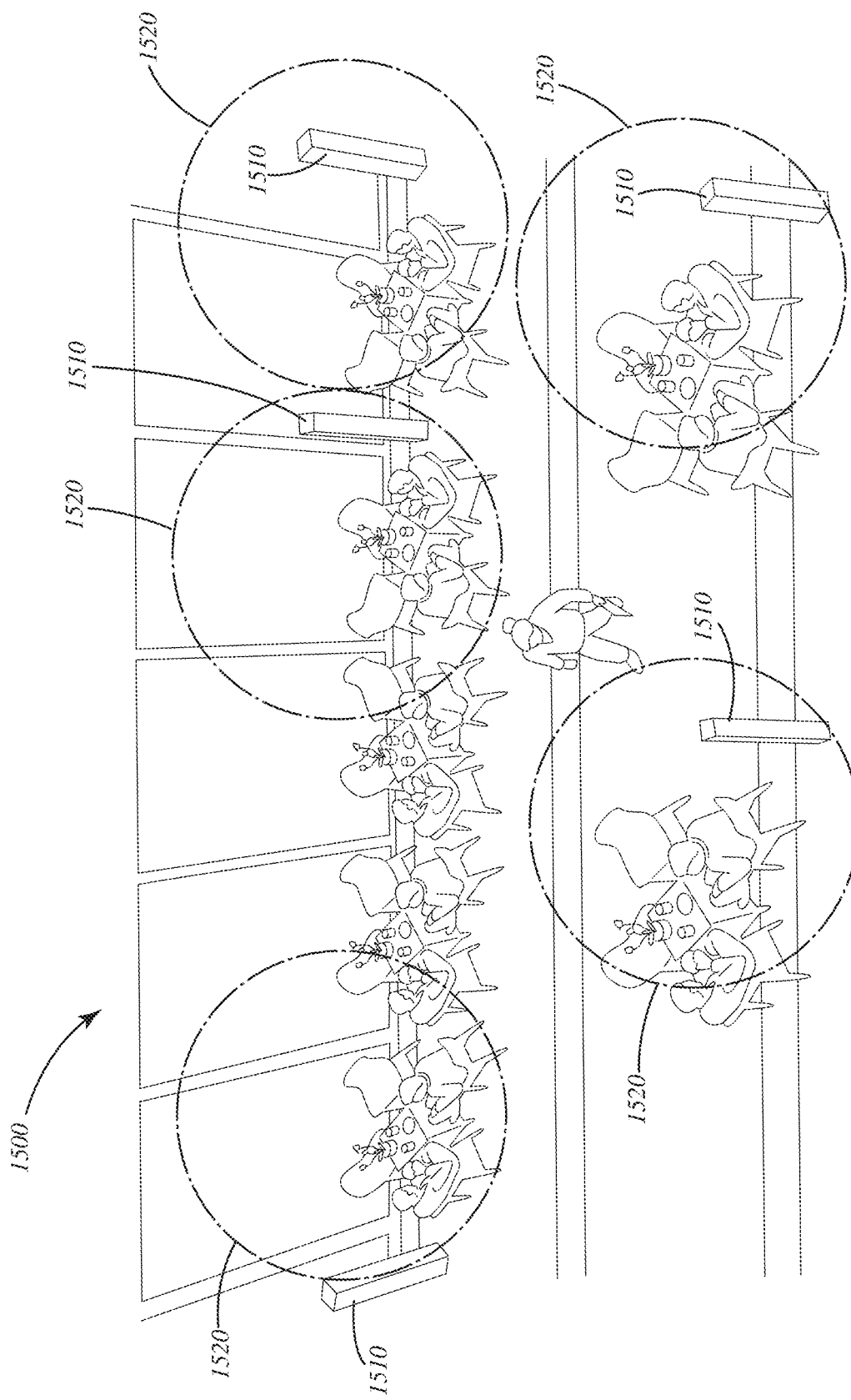
FIG. 15 shows an exemplary arrangement of portable pathogen reduction devices configured to cooperate as a dynamic air treatment system in a commercial environment.
Figure 16:
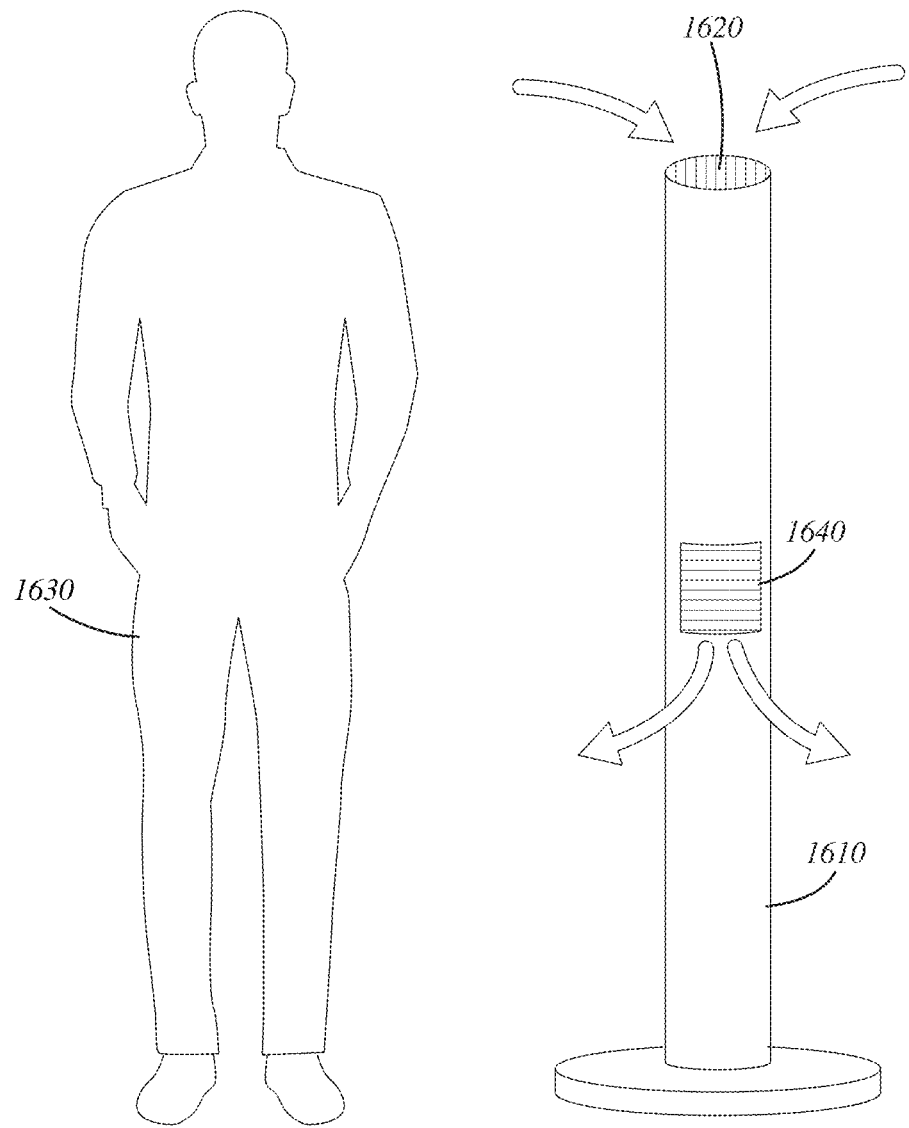
FIG. 16 depicts an exemplary telescoping air pathogen reduction device configured for treating air in a standing height zone.
Figure 17:
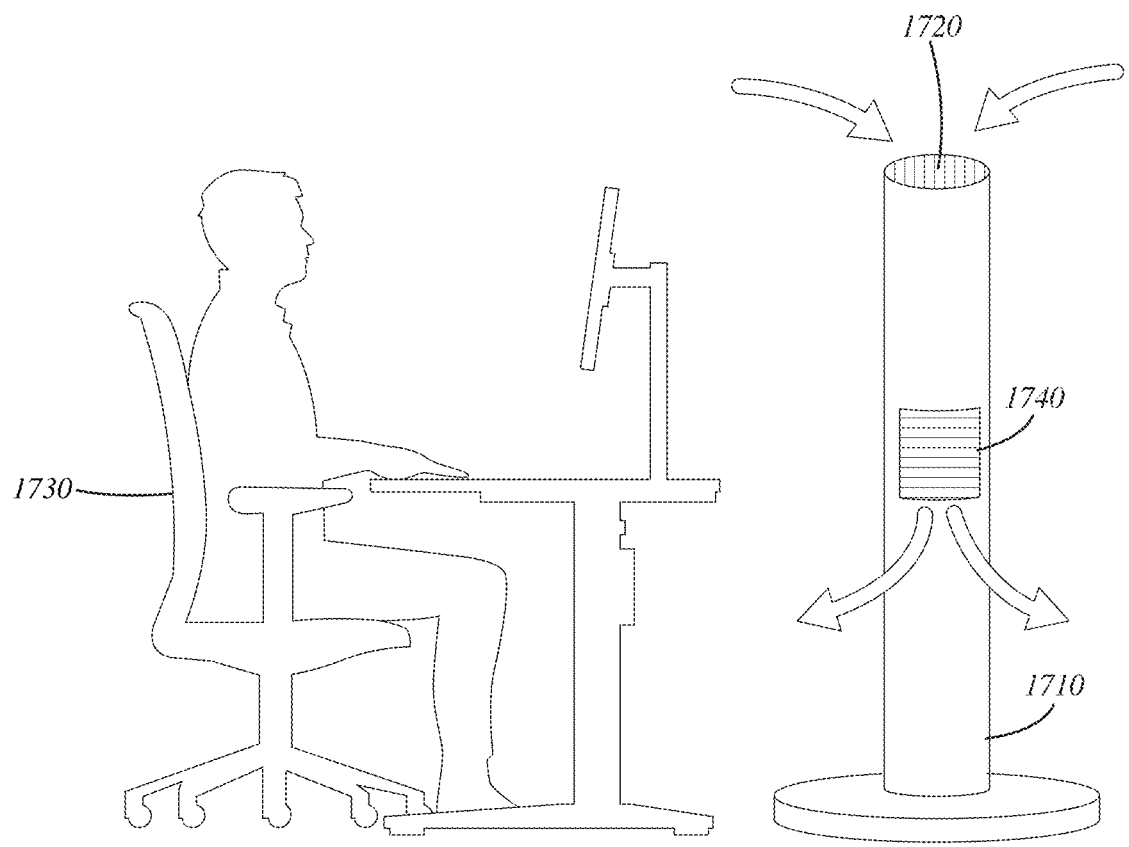
FIG. 17 depicts an exemplary telescoping air pathogen reduction device configured for treating air in a sitting height zone.
Figure 18:
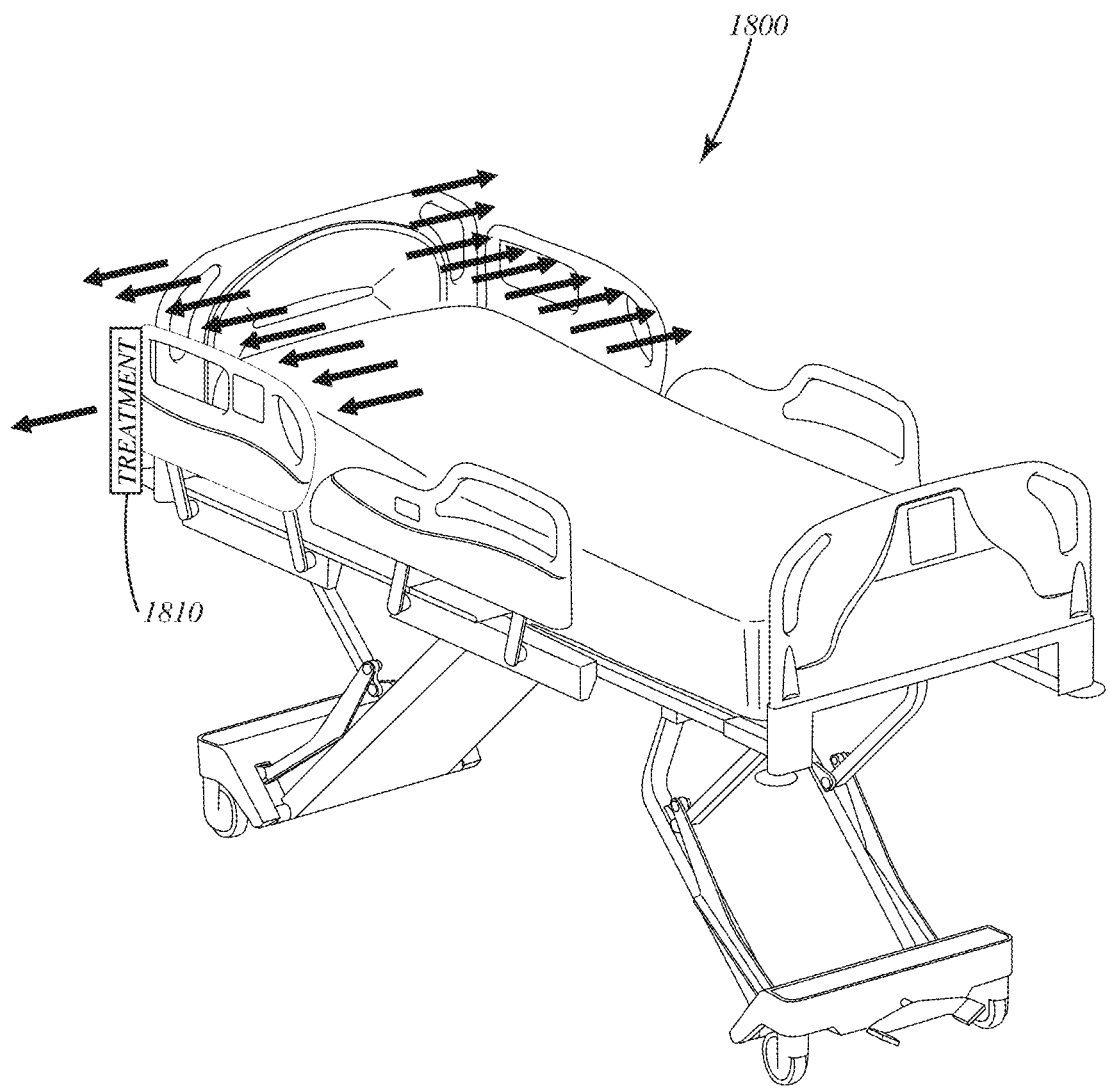
FIG. 18 depicts an exemplary hospital bed configured with a portable dynamic air treatment device.
Figure 19:
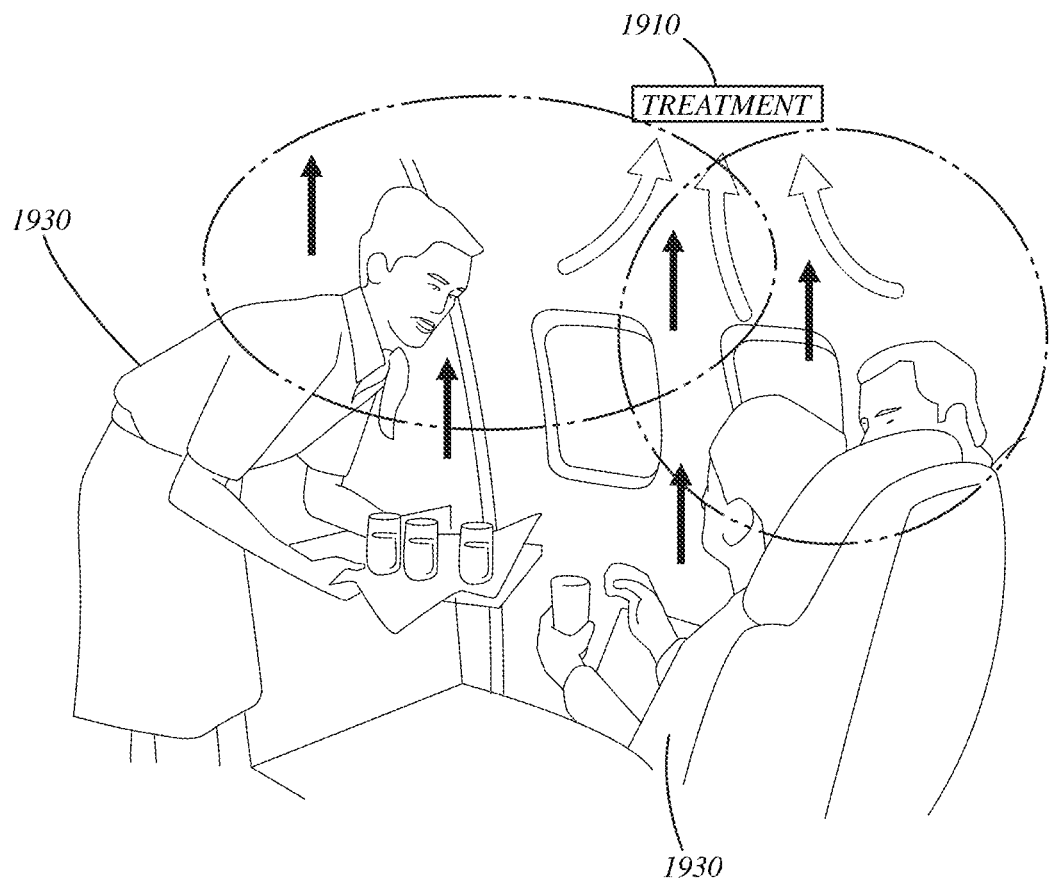
FIG. 19 shows an exemplary pathogen reduction device installed within a vehicle cabin.

Adjusting and applying power to the UV light source 160 at controlled intervals may allow the controller 236 to control the UV power output. This may enable frequent in-and-out occupancy for the room area 50 to be treatment compensated dynamically. It is not often ideal to run at the highest intensity as it impacts the UV light source 160 with shorter life. With a lower intensity operation, longer duration "on" cycle times (or dose times) may be targeted to obtain adequate disinfection as shown in FIGS. 14 and 15.

Dynamic control may be utilized to increase dose momentarily during busy times. Such dynamic control can be informed not only by the associated sensors based on a device level pathogen control protocol, but also by local level pathogen control and global level pathogen control instructions provided over a network based on local and global pathogen reduction protocols. A running average of busy times and target dose changes can be preprogrammed and the controller 236 may then modify these dynamically as presence iterations change with respect to the room area 50. This may be directed locally by the control 200 or by a cloud interface via a communication protocol.

An example of the algorithm involves first having a setting of the target dose. Each light fixture 100 may, for example, store a target dose in the form of intensity level and contact time at a calibrated distance for the room area 50. A communication interface 220 of the control system 200 may be provided to receive information from and transmit information to external electronic devices. For instance, the communication interface 220 may include a USB interface 242 (or other wired communication interface, such as Ethernet or RS-232) or a BTLE interface (or other wireless communication interface) that can be configured to allow external electronic devices, such as a smartphone, tablet computer, or other mobile electronic device to automatically write UV parameters and other relevant values into the control system 200.

In some applications, the UV light source 160 is fixed at the specific distance from the target disinfection surface and a UV-C intensity meter is used to assure dose for that interval. This can be used to assure that every device has been calibrated to preset standards. Some UV light sources 160 are manufactured in glass rather than quartz and will not emit UV-C. This type of quality and output calibration can be used in the field and in the production facility. The OEMs manufacturing the device can assure proper installation configurations over many mounting options and distances with a go-no-go answer for limits of performance.

The expected lamp life can also change dynamically as these minimum intensity expectations are set. An aging percentage may be added to account for source degradation over the expected source life. The dose data vs. power may be defined and measured in the lab first, stored and averaged over life and then verified at the surface in testing. The range or intensity span may be set and designed for optimal life for the UV light source 160. The starting calibration values include the span of intensity. This sets the range of time allowed and may be limited by UV exposure limits, such as eye contact thresholds. In the case shown, the thresholds are set by OSHA standards for UV-C contact and exposure.

Figure 4:
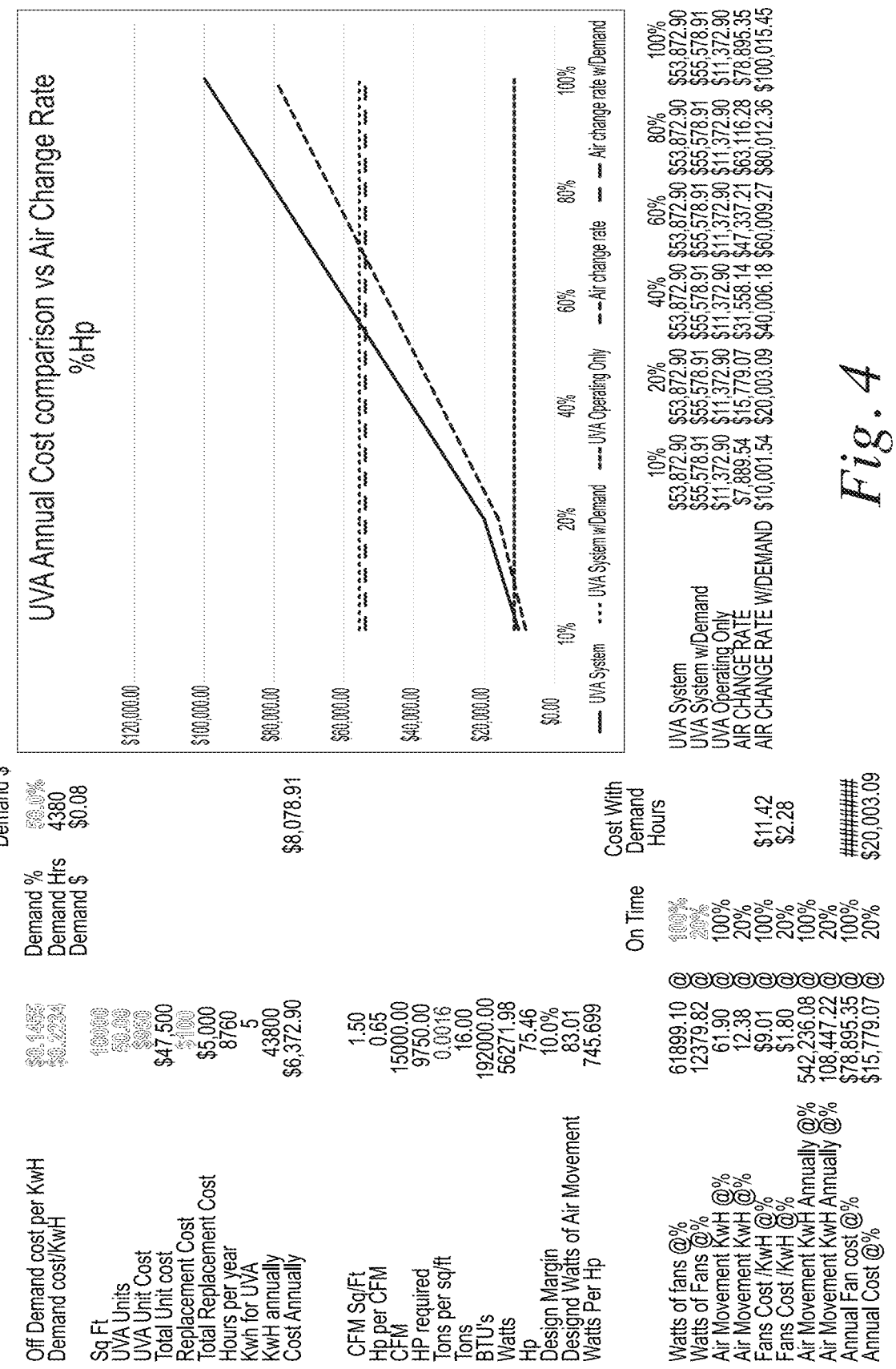
FIG. 4 illustrates a graph of cost comparison vs. air change rate and associated metrics.

The chart of FIG. 4 exemplifies the managed energy and replacement savings by having a managed biological system, such as a dynamic treatment system of the present disclosure, that takes power and maintenance into consideration. In one example we manage the electricity and consumable life (filters and lamps) as it relates to HVAC air exchanges having a beneficial biological reduction. As the chart shows the consumable life may be extended by as much as double the life or more while also reducing electricity consumption in half. It is important to note that the power is of secondary importance as the biological surveillance drive the outcomes. When people reduce numbers or leave a room, area, or building the dynamic treatment system can clean for the dwell time of the biologicals and then turn off. This process can be augmented by both a periodical and a monitoring of HVAC cycles in which case the system can initiate cleaning based on contiguous area and the events connecting that area.

In one embodiment, the communication interface 220 of the control system 200 has BTLE and/or Mesh capabilities. The mesh network can be Zigbee or BACnet to meet specific regulatory requirements or hospital specifications. In extreme monitoring solutions a cellular module 286 may be used to communicate the data to an external device (e.g., the cloud) as an alternative source of information gathering. As shown, the control system 200 may include transceivers and antenna matching circuitry 228 and a cellular module 286 that are coupled to corresponding antennas 252, 250, 254. The controller 236 may also have ports to allow directed wired connections, for example, using USB, Ethernet and RS-232 protocols.

In some applications, the control system 200 may have the ability to operate on battery power. The battery version may be provided with a battery 248, which may be the power source 152 for the light fixture 100. The battery-based system may be chargeable in a variety of ways, including wired and wireless charging configurations. The power storage may be sized for UV dose and interval and may be connected to charging equipment or directly chargeable. It may also have various indicators for providing feedback to a user.

As noted above, the UV light source 160 (e.g., UV-C lamp) may have an RFID tag 238 and the control system 200 may have an RFID reader 226 to understand when the UV light source 160 has reached end-of-life to encourage appropriate use and maintenance. UV light sources 160 often have a life based on a number of hours as they self-destruct due to the nature of UV light, including UV-C light. The control system 200, for example, through the controller 236, may keep track of lamp "on time" by reading from and writing to memory resident on the RFID tag 238. The control system 200 may adjust the actual "on time" by a correlation factor to compensate for lamp intensity. For example, the control system 200 may increment the lamp life counter by less than the actual "on time" for operation that occurs when the lamp intensity is reduced and may increase the lamp life counter by more than the actual "on time" for operation when the lamp intensity is increased. The correlation factor (or intensity adjustment factor) may be provided by the lamp manufacturing, may be determined through tests of the UV light source 160, or may be estimated based on past experience.

The communication interface 220 of the control system 200 may also have USB and Power over Ethernet ("POE") circuitry 237, which may enable usage without additional power cord requirements for this equipment. In one embodiment, the power management circuitry 239 may allow inputs from power generating sources and various voltages enabling flexible power adaptation. For instance, the power management circuitry 239 may allow AC power to pass through so that the host piece of equipment is undisturbed. When the light fixture 100 is integrated into another electronic device, the power management circuitry 239 may allow the light fixture 100 to draw power from the power supply for the host electronic device as the power source 152. A single outlet can be used to avoid potential confusion when plugging in the device. The power management circuitry 239 may be operable to power from a variety of sources, including wireless, USB, DC, and battery sources. In one embodiment the power regulation is done in a buck boost manner to provide an energy harvesting power supply that produces a regulated power source when voltage is produced by various power sources.

The control system 200 in the illustrated embodiment may include regulator circuitry 246 configured to facilitate operation of the UV light regulator 120. The regulator circuitry 246 may include a motor controller and sensor circuitry. The motor controller and sensor circuitry may drive and monitor motor RPM of one or more fans. The motor controller may control the speed of the one or more fans, such as by adjusting a duty cycle of a PWM drive signal supplied to the one or more fans. The sensor circuitry may monitor current against a target and/or range of currents associated with a target RPM of the one or more fans.

The regulator circuitry 246 may also include UV light regulator sensor circuitry 256, which is shown separate from the regulator circuitry 246 in the illustrated embodiment but may be incorporated therein.

The motor controller of the regulator circuitry 246, as discussed herein, may be operable to control an amount of UV light directed into the room area 50 of the room. The motor controller may be a DC motor controller operable to supply power to drive a motor of the UV light regulator 120, which may move a movable component of the UV light regulator 120 to selectively increase or decrease an amount of UV light directed into the room area 50.

The UV light regulator sensor circuitry 256 may be operable to provide feedback indicative of at least one of a position of the movable component and an amount of UV light being directed into the room area 50. For instance, the UV light regulator sensor circuitry 256 may include a UV-C light sensor operable to provide a value indicative of an intensity of UV-C light being directed into the room area 50. The intensity value may aid in determining positioning of the movable component of the UV light regulator 120 to achieve a target level of UV light applied to the room area 50. The UV light regulator sensor circuitry 256, in one embodiment, may include an encoder (e.g., an optical encoder) indicative of a position of a motor shaft or the movable component, thereby being indicative of an amount of UV light being applied to the room area 50.

In one embodiment, as discussed herein, the control system 200 may include a room sensor interface 255 operably coupled to the controller 236. The room sensor interface 255 may be configured to provide feedback indicative of whether the room area 50 (potentially the entire area of the room) is occupied by one or more persons. The room sensor interface 255 may be configured to count people or track the number of people within the room area 50. Alternatively, feedback from the room sensor interface 255 may be used by a controller separate from the room sensor interface 255 to count people or track the number of people within the room 50.

In the illustrated embodiment, the control system 200 may use feedback from the room sensor interface 255 to determine whether to direct UV light into the room area 50, or to discontinue providing UV light into the room area 50.

It is to be understood that the room sensor interface 255 may be separate from the control system 200 in an external device capable of communicating information indicative of presence of one or more persons in the room. For instance, the room sensor interface 255 may be a motion sensor (e.g., a PIR sensor) capable of sensing the presence of one or more persons in the room or room area 50. This motion sensor may communicate wirelessly with the control system 200 or with an intermediary device capable of relaying occupancy information to the control system 200. Additionally, or alternatively, the room sensor interface 255 may include a switch coupled to a door of the room to indicate a status of the room as being open or closed, using this information as an indicator of whether the UV light source can be activated for disinfection of the room area 50. For instance, if the door is determined to be open, activation of the UV light source 160 may be prevented in order to avoid leakage of UV light outside the room area 50.

The control system 200 may include a visible light driver 245 separate from or provided in the visible light module 180 to facilitate directing operation of a visible light source.

The visible light driver 245 in the illustrated embodiment may also include a user interface (e.g., an ON/OFF switch, a brightness adjuster, and a color adjuster) operable to allow a user to control operation of the visible light source. For instance, the user may utilize the user interface to direct the visible light driver 245 to increase or decrease a color temperature of the visible light source. The visible light driver 245 may include a controlled current source and/or a controlled voltage source to supply power to the visible light source in accordance with a target operative mode of the visible light source.

Operation of Dynamic Treatment System. Exemplary operation of a dynamic treatment system within the context of a building will now be described in connection with FIGS. 5-8. To aid in explaining operation of the dynamic treatment system, FIGS. 5-8 illustrate several views of an exemplary building floorplan 500, 502, 504 depicting the relative positions of pathogen reduction devices 510 and associated treatment zones 520, 522, 524 as well as sensors 512, 514, 516. FIGS. 5-8 also illustrate various operating modes of pathogen reduction devices for several different situations showing how the dynamic treatment system reacts to various changes in the building environment and adapts at device, local (room), and global (building) levels.

In the depicted embodiment, the pathogen reduction devices 510 and sensors 512, 514, 516 are distributed throughout the building and collectively form at least a portion of the dynamic treatment system. The pathogen reduction devices 510 can be permanently or semi-permanently installed as building fixtures or be portable pathogen reduction devices that are strategically and movably placed throughout the building. A building floorplan for one exemplary building is depicted in FIGS. 5-8 to illustrate various aspects of the disclosure, but it should be understood that the dynamic treatment system can encompass multiple floors and essentially any type of building, regardless of the specific floorplan. Further, while the floorplan is helpful to understand operation of the dynamic treatment system—no such visual representation of the floor plan need be maintained by the system nor presented to a user. In some embodiments, a visual representation of the various coverage, status, and protocol levels, plumes, or other information, may be presented (e.g., graphically, or textually) to a user device via a network connection to the dynamic treatment system or a cloud server hosting appropriate data.

As depicted in FIGS. 5-8, each pathogen reduction device 510 can be associated with a treatment zone 520, 522, 524. The size and shape of the treatment zone may be derived based on the specific pathogen reduction device, its mode of operation, and/or the building architecture in proximity to the device. Some pathogen reduction devices can be configured to operate in a normal mode, medium mode, or high (may be referred to as maximum) mode. These modes of operation generally correspond to one or more pathogen reduction device settings, such as UV bulb intensity, dose time, delay time, or essentially any other adjustable pathogen reduction device setting that effects the effectiveness of the pathogen reduction device.

As will be discussed in further detail in connection with later examples, the pathogen reduction devices can operate based on a schedule, user presence/occupancy, people counting, light level, particulate loading, or any other suitable trigger condition.

Figure 5:
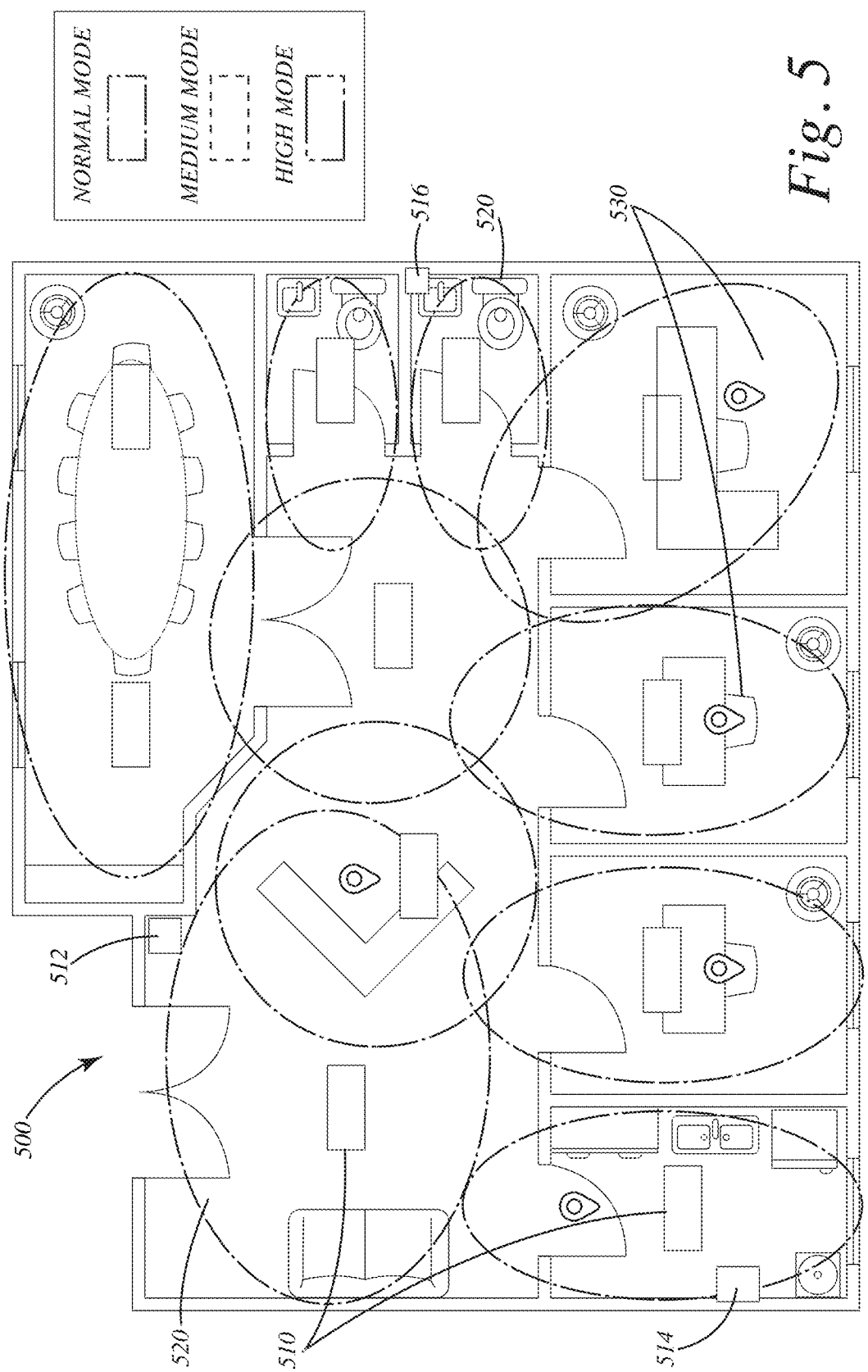
FIG. 5 illustrates a visual representation of operation of various pathogen reduction devices within a dynamic air treatment system according to a first exemplary scenario.

FIGS. 5-8 also depict icons representing human activity. Specifically, markers 130 showing human activity are illustrated on the maps 500, 502, 504 in FIGS. 5-7. The number of markers represent a relative amount of human activity in that area. In FIG. 5, five different rooms have a single marker 530 indicative of a low amount of human activity. This human activity may be tracked by sensors 512, 514, 516 in communication with the dynamic treatment system. The various sensors that can be utilized in connection with the dynamic treatment system are discussed at length elsewhere in the application, suffice it to say, the sensors can include people counting sensors, touch sensors, passive or active infrared sensors, or communication from a user's mobile phone to name a few examples. More dense human activity, for example as determined by a people counter sensor 512 or the like, is illustrated with multiple markers, such as illustrated in treatment zone 522 in FIG. 6, which has three markers 530. Even higher density can be represented with more markers, such as in the conference room covered by treatment area 524 that includes six markers 530. The markers 530 can represent humans one to one or represent a general human density/activity level in that area according to one or more sensors.

The various pathogen reduction devices 510 can operate based on a device level pathogen reduction protocol, a local level pathogen reduction protocol, and a global level pathogen reduction protocol. In some embodiments these device, local, and global pathogen reduction protocols can correspond to normal, medium, and high modes of operation for a pathogen reduction device and be triggered based on the human activity level within the treatment zone associated with that pathogen reduction device. For example, where the human activity level is below a threshold, each of the pathogen reduction devices 510 can operate in its normal operating mode according to its device level pathogen reduction protocol, which is associated with a configuration or set of pathogen reduction parameters that provide effective pathogen reduction while balancing the strength of pathogen reduction and energy expenditure of the pathogen reduction device. As human activity within the building increases (or is expected to increase), the pathogen reduction devices 510 can change their mode of operation as depicted and described in connection with FIGS. 6-7.

The dynamic treatment system can include coordinated control between multiple pathogen reduction devices 510 that can be informed by sensors 512, 514, 516 or other information sources. The control can be administered by a dynamic treatment system controller. The dynamic treatment system controller can be a controller disposed in the cloud that communicates over the Internet to the pathogen reduction devices 512 disposed in the building, installed locally within the building, or one of the pathogen reduction devices can include or act as the dynamic treatment system controller.

Figure 6:
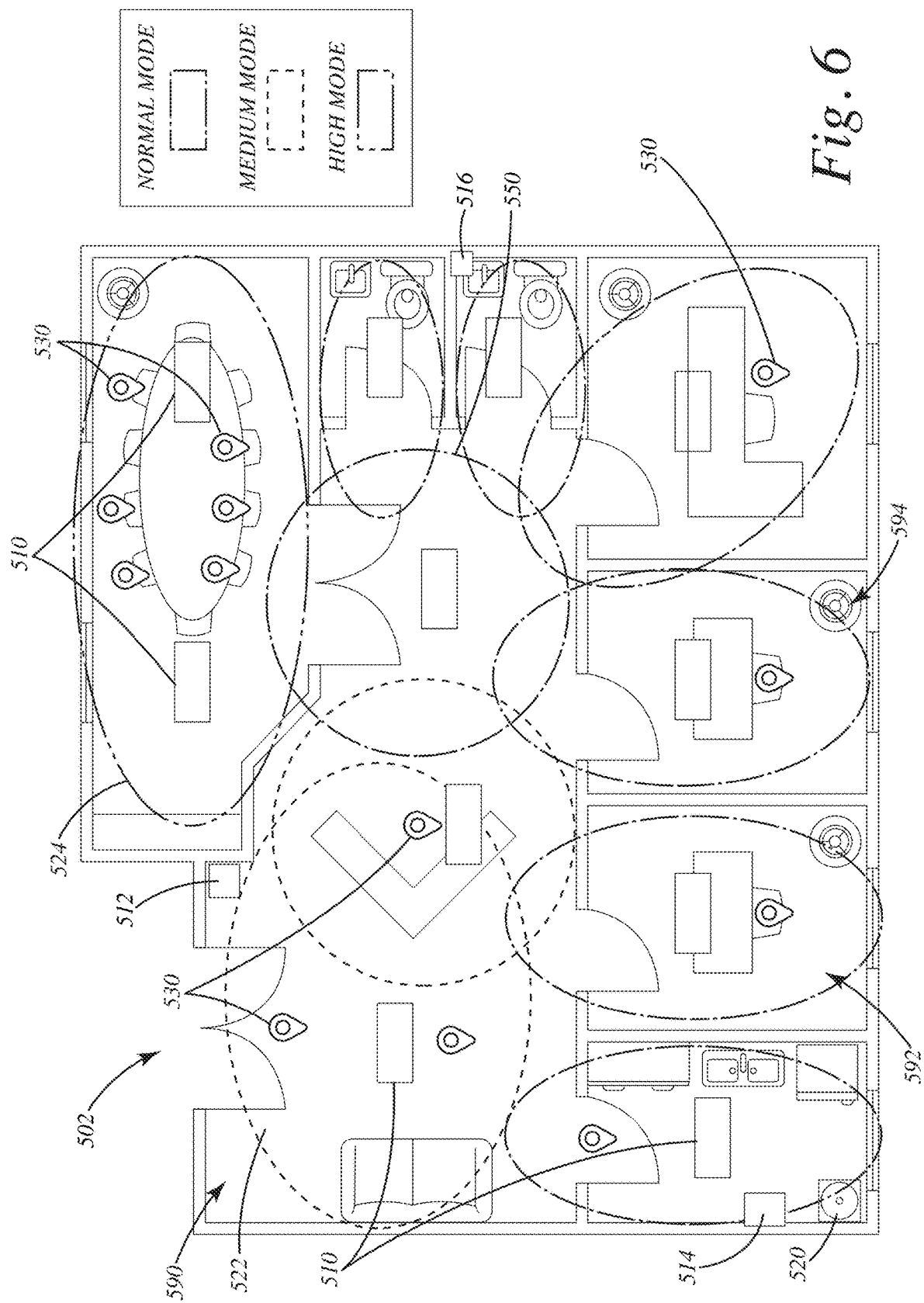
FIG. 6 illustrate a visual representation of operation of various pathogen reduction devices within a dynamic air treatment system according to a second exemplary scenario.
Figure 7:
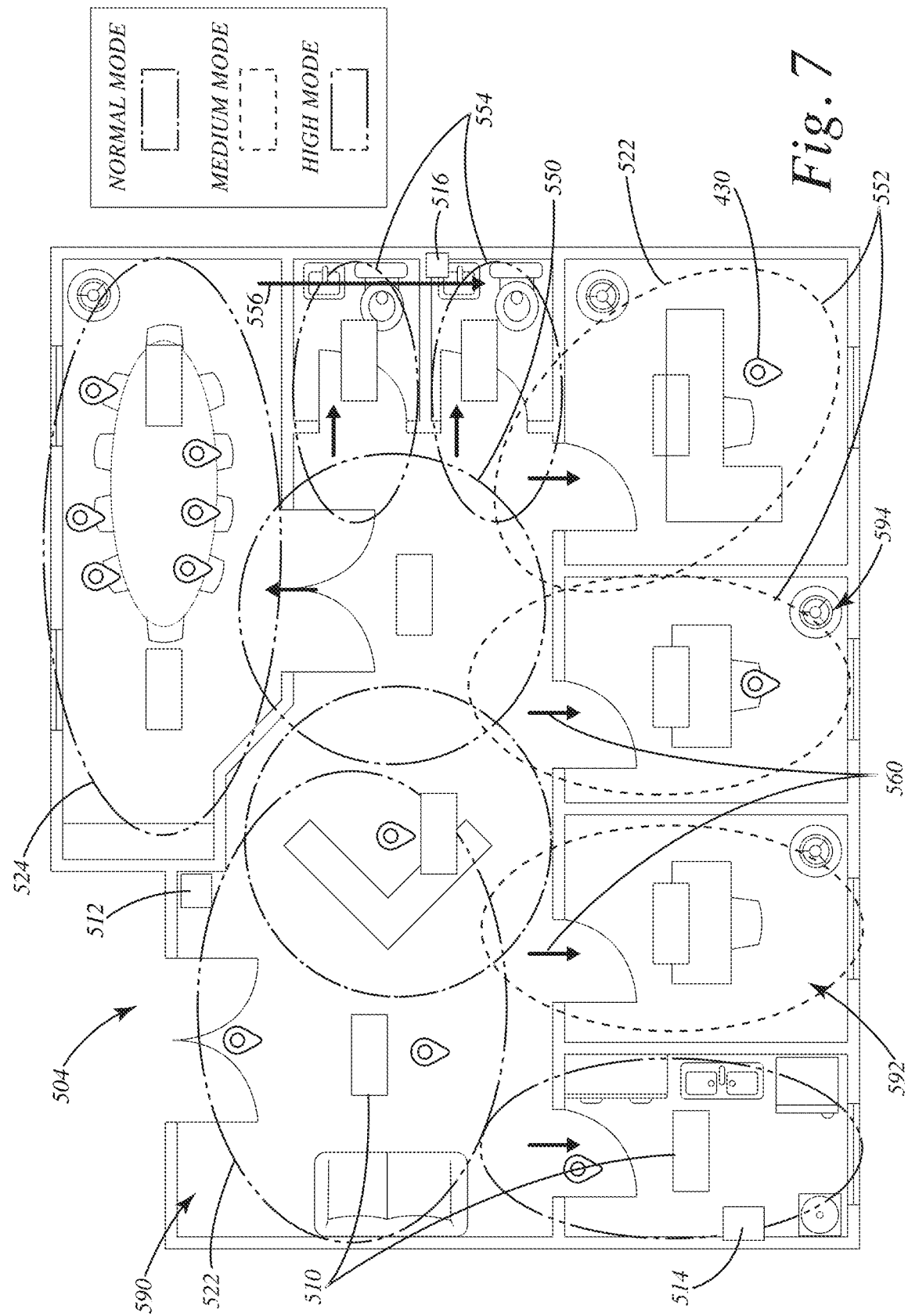
FIG. 7 illustrate a visual representation of operation of various pathogen reduction devices within a dynamic air treatment system according to a third exemplary scenario.

FIG. 6 illustrates an exemplary response of the dynamic treatment system to a particular biological loading. In the depicted embodiment, the different treatment zones 520, 522, 524 represent different modes of operation of the pathogen reduction devices associated with those zones. One treatment zone 524 provided in a conference room with high human activity level is provided by operating the two associated pathogen reduction devices 510 in the conference room in high mode. Another treatment zone 522, provided in a large lobby area with medium human activity level (three markers 530) is provided by operating the two associated pathogen reduction devices 510 in the lobby area in medium mode. The remaining seven other treatment zones 520 have a low human activity level and therefore the associated pathogen reduction devices are operating in normal mode. Put simply, the different levels of treatment represented by the depicted different treatment zones 520, 522, 524 can be provided by operating the associated pathogen reduction devices in different modes of operation that correspond to providing the different treatment levels. Further, it is worth noting that the various pathogen reduction devices 510 can be different types of pathogen reduction devices, e.g., one of the devices 510 in the conference room with treatment zone 524 may be an air treatment system and another device may be a surface treatment system.

A variety of methods can be used to determine occupancy within the building as a whole as well as the specific areas surrounding the pathogen reduction devices 510 of the dynamic treatment system. In one embodiment, the threshold occupancy for one of the pathogen reduction devices 510, such as a dynamic air treatment system in the conference room covered by treatment zone 524, to move from a normal mode of operation to a medium mode operation and from a medium mode of operation to a high mode of operation may vary depending on a variety of factors, including, for example, the size of the room containing the dynamic air treatment system and/or the number of dynamic air treatment systems in a given space. That is, the threshold occupancy to trigger moving from normal to medium or medium to high mode can be programmed according to data provided by an occupancy sensor or other data indicative of occupancy, as well as the size of the room/treatment zone, and the number of treatment/pathogen reduction devices.

This dynamic treatment system configuration represents one method of operation where the human activity level is tracked at a local or room level and the sensors associated with a particular locale are informed about the local human activity level and adjust their operation accordingly. However, utilizing local occupancy sensor information is not the only basis for adjusting system operation. The dynamic treatment system can recognize occupancy and make adjustments locally at a room level that leverage cooperation between the pathogen reduction devices in that room accordingly, however, the dynamic treatment system is not limited to those adjustments. The system can be configured to recognize and respond to airflow paths within the building.

FIG. 7 shows another response to the same exemplary biological loading of the building as FIG. 6. Although the occupancy is generally the same throughout the building, the dynamic treatment system in this embodiment is configured to handle the biological loading differently. In this configuration, the pathogen reduction devices 510 are coordinated globally to provide a building level response. That is, the pathogen reduction devices respond to the particulate loading or particulate flow in the building. As before, pathogen reduction devices in areas with increased human activity are configured to operate at higher intensity to reduce pathogens. However, in this embodiment, other pathogen reduction devices in areas of the building that do not have such increased human activity are also configured to operate at a higher intensity level according to a global pathogen reduction protocol. Specifically, the pathogen reduction device settings can be dictated not only by the amount of human activity near the pathogen reduction device or within the local area of the device (e.g., within the room), but also by the relationship, e.g., spatial or airflow relationship, between the area the device resides and the rest of the building.

By way of example, the relationship between a dynamic treatment system device (e.g., a pathogen reduction device or a sensor device providing pathogen factor data) and the other system zones (e.g., areas/rooms of the building) can be determined in several different ways. One way is for each pathogen reduction device to be assigned to a room within the building and for the rooms to be associated by way of air flow path(s) between the rooms. The airflow path(s) between two rooms can be measured by monitoring pressure levels in each location and comparing the results, globally high to low pressure areas indicate probable airflow to adjacent areas. This technique can be utilized to store air flow data about the airflow of a building in terms of its rooms by positioning airflow sensors within each room. In some circumstances, the layout and airflow paths of a particular floorplan can be extrapolated from a collection of airflow sensor devices distributed throughout the building without having an individual airflow sensor in each room of the building. Further, in some versions of the system, multiple airflow sensor devices can be included within a room of a building and can enable not only global inter-room airflow mappings, but also intra-room airflow mappings based on the pressure level data. This is one example of sensor data that can be leveraged by the dynamic treatment system to enable the system to execute a global pathogen reduction response protocol to add a layer of protection for the rooms within a building. That is, the overall system treatment level can be adjusted or set based on the pressure differentials between the different pressure level sensors and their locations within the building. In some circumstances, if the pressure levels indicate an unusually high airflow, the system can be set to a maximum treatment level, whereas if the pressure levels indicate an unusually low airflow, the system can be set to a minimum treatment level. Of course, many other factors can also factor into the ultimate system decision about where to set or adjust the treatment level.

To provide a more detailed example, referring to FIG. 7, airflow paths 560 between adjacent rooms can be defined in terms of the direction and strength of airflow from one room to another. The airflow paths can be tracked in a database as vectors or another form of information. An airflow path 560 can represent the total net airflow from one room to the next in terms of average airflow from one space to the other—this can include airflow due to the doorway, vents, or essentially any other airflow path between the two rooms. In some circumstances the airflow path can be circulating and there may be both airflow vector representing airflow from one room to the other as well as a separate airflow vector representing airflow leaving that room and flowing toward the other room. The airflow information can be collected during a calibration or initiation stage and stored in memory to be used by the global pathogen reduction protocol or may be monitored and dynamically changed in real-time, near-real time, or periodically (e.g., monthly).

This airflow path information can be utilized to inform pathogen reduction devices in adjacent rooms. For example, the pathogen reduction device(s) within the treatment zone 550 adjacent to the conference room treatment zone 524 can be elevated to operate in high mode (or at some other appropriate pathogen reduction device configuration) instead of normal mode. In addition, the pathogen reduction devices in treatment zones 554 that are connected by a vent airflow path 556 to the high density human active area can also be switched to high mode since they may be categorized at a higher pathogen risk due to the airflow path, which includes flow from the adjacent room associated with treatment zone 550 as well as directly from the room with treatment zone 524 by virtue of an air duct. Put another way, the dynamic treatment system controller can be configured to step up the operation of the pathogen reduction devices in the dynamic air treatment system in the regions corresponding to the treatment zones in commons areas 522, 550 and adjacent areas 554, 552 to medium mode or high mode to assist in cleaning and mitigating the air to account for the change in biological load. However, where the proximity to the high-density human activity is lower, the amount of change in the mode of operation can be reduced—e.g., pathogen reduction devices for treatment zones 552 are only raised from normal mode to medium mode whereas pathogen reduction devices for treatment zones 550, 554 that are more proximal to the high-density human activity treatment zone 524 in this example are raised from normal mode to high mode.

The ability for the dynamic treatment system to access to information about the particulate flow or airflow paths within a building allows pathogen reduction devices to work more effectively, expending energy to treat higher risk areas and conserving energy by not over treating lower risk areas. This particulate flow can be sensed by the system in a variety of different ways.

In some embodiments, the particulate flow for a building can be obtained by monitoring pressure levels at various locations within the building. That is, by monitoring pressure with sensors, directly or indirectly, the dynamic control system can obtain information about airflow traffic around the building, e.g., on a room-by-room basis, and trigger local and global responses based on that information. For example, to the extent a pressure sensor identifies a first pressure level in an area and another pressure sensor identifies a second pressure level in an adjacent area, the dynamic treatment system can monitor the relative changes in pressure level, e.g., tracking the pressure equalizing between rooms when an air pathway is created between the rooms such as when a door between the two rooms opens. This monitoring can be scaled to obtain pressure information about the various rooms within a building and to understand the airflow from room to room within the building in general. As another example, output from a door sensor and a pressure sensor for the room with the door can inform pressure changes in adjacent rooms based on the door opening and closing events. That is, other sensors can supplement or stand-in for pressure sensor data that can enable tracking air flowing at a room level within a building. By monitoring pressure changes (directly or indirectly) and related activities the control system can track the epicenter of an event and the subsequent ripples and impact. For example, opening a conference room door may result in a pressure equalization and associated airflow between those rooms, but it also may result in further pressure equalization to other rooms, which can cascade to other adjacent rooms.

Pressure equalization or pressure movement events can also allow the control system to infer proximity and adjacencies between monitoring units. It may be completely open space between units or there may be an air pathway through one or more doorways or vents and that can also be tracked, e.g., by virtue of intermittent, proportional equalization or tandem movement. In general, tracking these changes over time (intermittent and averages), the control system can generate and store in memory a tree of pressure information, such as pressure performance in one or more adjacent area(s) that can inform dynamic control system decisions, e.g., triggers for the local and global pathogen reduction protocols. This can essentially be used to provide output to a function such as pressureSnapshot( ) which can provide a current "snapshot" of the pressure levels within the building at that moment. Historical data can also be maintained and recalled using that functionality. Movement, occupancy, HVAC operation, or other activities can be assigned or attributed to the pressure changes over time. For example, the system can obtain pressure snapshots with no occupancy and over various activity levels to build a comparative base of information. The pressure snapshot tree generated within an adjacency can determines an order and priority of control within that adjacency. For example, high to low pressure transitions can be treated by the control system as high priority as airflow tends to travel from the high-pressure area to low pressure adjacent areas.

Occupancy or people counting sensors can be utilized by the dynamic treatment system to monitor building and/or room occupancy. By utilizing a sensor to directly or indirectly count the number of bodies in a particular area of the building, and the changes to that number, estimates about the movement of occupants about the building can be made, which can be used to inform control decisions, including local and global pathogen reduction protocol triggers. Tracking people counts and movement of people about an environment are useful tools because both represent opportunities for contamination (e.g., density of human activity generally correlates to an increase in pathogens and human movement about a space generally correlates to pathogen spread). If suitably tracked, people count information and/or movement information can drive the performance settings locally (e.g., at a room level among multiple pathogen reduction devices within a room), but also globally (e.g., at a building level across multiple different rooms that have pathogen reduction devices) to adjust the coordinated system. The occupancy information can also be used for security, lighting control, and power control, if desired. For example, locally the dynamic treatment system can be configured to treat a given area within a given period of time. Accordingly, the occupancy information can be utilized to build a schedule of occupancy to inform and track timing. The system can turn on in time to have cleaned the environment startTime( )–cleanTime( ) and to have a fully scrubbed environment before people start. Likewise, running the system 24/7 can increase maintenance needs and reduce device life, accordingly, the system can be configured to control on-time and energy costs, especially during low occupancy windows. Further, the system can use occupancy to determine weekly schedules and set a dynamic operating schedule for the pathogen reduction devices. For example, off time can be set as endofday( )+cleanTime( ) where a given pathogen reduction device is shut off after the designated cleaning time has been reached. Other factors that can drive contamination such as pressure levels, particulate levels, and HVAC operation can override the start and stop criteria and be reported to an administrator via a dashboard, e.g., at a computer or personal device.

Due to airflow and turbulence, particles move about a space and generally eventually settle on various surfaces over time. In many environments such particles are eventually disturbed and recycle. People, cleaning, construction, and the environment in general all have the capacity to impact the monitored particulates. The system can establish a particulate baseline within an environment and watch the numbers over the cleanTime( ) without people present to judge a range of performance. As people walk, move and interact data about the change in particles over time can be collected from the measurements. For example, a relative average change in particles over time can be tracked. If the number of particles rises above average the control system can be configured to adjust mitigation strategies at a device, local, or global level for any particular pathogen reduction device. In some systems and methods, a particulate tree over time can be generated and stored in memory to describe plume movement within an environment, such as a building.

Operation of the HVAC and pressure differentials may be used to aid the particulate sensor information and particulate tree.

A tree, such as a particulate tree, can be maintained in memory that stores adjacency information for use in the local and/or global pathogen reduction protocol. That is, the dynamic treatment system can maintain an adjacency table, that can be utilized to generate a particulate tree, pressure tree, or other form of tree for tracking airflow, pressure, or particulate movement within a space such as a building. IN some embodiments the adjacency table can be supplemented with data to form a tree or other data structure to track flow information over time. In the adjacency table, units that change together, e.g., have a correlation, can be marked, or linked together as being potential adjacency. For example, areas connected by a vent, doorway, or common space typically will have similar flow information—or at least correlation between flow information such as airflows, particulate flow, and pressure values. Iterating these connections provides a tree-like structure for tracking flow information, which can be accessed and utilized for software monitoring purposes. A second adjacency list can be maintained based on the physical building configuration. That is, the second adjacency list can denote actual recognized physical adjacencies, including doorways, hallways, vents, and other airflow paths within the building. This adjacent list can be derived from user input into a user-interface or from a floorplan analyzer that accepts a floorplan file or image data related to the building. The hierarchy of the control of the dynamic treatment system can be at the device level, then local based on the $1^{st}$ adjacency, local based on the $2^{nd}$ adjacencies, and then globally to impact pathogen reduction. The first adjacency can be based on the physical room layouts, while the second adjacency can be based on contiguous connections and interface between spaces.

The building configuration can refer to the various physical adjacencies created by the building structure and its various states. Doors may be left open or closed but understanding the nature of the construction the system can be configured to interact and monitor probable and improbable conditions allowing the system to better understand the environmental impacts of various conditions. The configuration selections can include positioning various sensors throughout the building, positioning, and deciding how many pathogen reduction devices throughout the building to install in various rooms and collecting various datasets in various configurations.

The dynamic treatment system can include various devices and product solutions. The devices included in the system may be portable, installed hardware, HVAC oriented, building controls and sensors or other associated devices. These devices may be durable or have consumable elements. Operation of both the durable and consumable elements over the complex usage and performance criteria can be monitored.

The system can assess time-based interactions and adjust via the device, local, or global pathogen reduction protocols. The dynamic treatment system can monitor and adjust based on people movement, e.g., within a building. Such movements typically have a large impact on source contaminates. By tracking occupancy and people counting the system can track information regarding volume and areas of interest over time. By cross-referencing such information with settling times, HVAC schedules, and people schedules the system can begin before people enter the environment and end once the systems have reached a point of reduced or no additional efficacy. This can save energy and preserve system life, which can reduce or minimize maintenance. The off time can be represented by the formula:

$$OffTime(\ )=lastOccupancy(\ )+settleTime(\ )+cleanTime(\ )$$

As mentioned above, additional HVAC activities or particulate plumes of pressure changes may override a planned event.

Given airflow cycles and pressure changes the system can track the time to accumulated settled surfaces, i.e., settleTime( ), and the distribution of particulates to settle particleDist(x,y). The timing can vary based on air movement and people movement. Settle time can generally refer to times when the space is not being used or being used a reduced amount.

Energy. For times where the system aims to reduce or minimize maintenance, the system can be configured to allow energy to drive the performance setting, on and off times, and can also enable what factors, if any, can override such settings. An associated list of factors that are part of a checklist that can be utilized for determining an energy or pathogen driven profile. Both approaches can be appropriate depending on the environmental performance and biological surveillance.

Sound. By monitoring sound levels or other sound information, the system can track its own diagnostics. Specifically, by turning the fans on and off while monitoring the sound. For example, diagnostic information can be determined by listening, e.g., with a microphone in communication with the dynamic treatment system, to a steady ambient sound, turning on the fan and then monitoring and verifying ambient( ) sound levels again. This can also be utilized to monitor ambient sound levels within an environment. The fan can be shut off to take a measurement (i.e., ambient( )), then a second measurement with the fan on can be taken (i.e., ambient&fan( )). The ambient level can be utilized to set thresholds for acceptable upper-level fan speed. The acceptable ambient sound levels can vary depending on the number of people in the environment—for example, if there are more people in an environment, generally a higher fan speed can be allowed. The acceptable fan speed can be user or system adjustable based on the ambient sound levels. Further, the fan speed can be configured to automatically track to changes in the ambient sound level so as to not draw attention to the pathogen reduction process. This can be user selectable and configurable both in a local mode and adjacency mode. If a local device is commanded or requested to be quiet, the system can be configured to become more sensitive to ambient sound in the adjacent units as well and may adjust fan speeds or other components accordingly for some period adjustSound( ) or always maxSoundThreshold( ).

Building control. The building control system can track and utilize various systems including occupancy, lighting controls, HVAC zones. This can provide the system with additional information to enhance energy consumption, on times, and potential down time programming.

HVAC Interaction. Some dynamic treatment systems can be configured to work with HVAC systems, e.g., via an exchange of commands or requests or other communication. By tracking information relating to HVAC operation, such as settings and operational directives, the dynamic treatment system can track the progress of the HVAC changes through the system to better understand adjacencies, air flow (outlet to device) and timing of propagation through the system (build(device2deviceTree( )). This tree like structure provides information about the air movement and propagation of the adjacency and global changes over time.

Temperature & Humidity. The dynamic treatment system can be configured to track temperature and humidity information. For example, by tracking temperature in degrees by day along with humidity levels, the system can assess and predict when conditions are set or will be set for various species/pathogens to thrive and can make adjustments to account for the situation at the appropriate time and in the appropriate amount. Certain insects, molds, fungi and bacteria need specific conditions for specific periods to sporulate or reproduce. The additional data of temperature and humidity can help the system to identify natural adjacencies as these change in time. This also allows the monitoring of HVAC propagation throughout a building. For example, the rate of change over time over the monitoring devices can provide information about the propagation time of the system response. The temperature and humidity in the upper air systems can be indicative of the effect of people gathering as the heat and humidity rises and can be utilized to drive higher speed control locally if above the present ambient thresholds. An example would be IF(ambient&h( )>=t&hthreshold( ))fanSpeedAdjust( ). The temperature and humidity can be monitored and utilized to represent breathing zones with a space as well. For example, as the humidity and temperature rise in a specific area, the system can determine that it is due to people gathering and the thermal rise of breathing and humidity in that area. This can trigger a differential in that adjacency which in turn can change the pathogen mitigation strategy by changing fan speed or other pathogen reduction parameters in the system.

Movement. People movement is one driver to source contamination. The more people moving the more potential pathogens stirred up and/or deposited by people. One aspect of the dynamic treatment system relates to prediction and tracking of source contamination movement. Occupancy sensors, to the extent available in the system, can be utilized to obtain information about movement of people locally within an environment. Further, output from multiple occupancy sensors can be utilized to obtain information about movement of people globally within the building. That is, globally this information provides the control system with a perspective of active areas where people are moving. While taking particulates into consideration movement threshold can be engaged to see where and when an average movement rates climbs above a threshold and the treatment can be adjusted accordingly, accounting for adjacency. An example can include a calculation as follows:

IF(actualMovement( )>=avgMovement( ))fanSpeed-Adjust( )

Usage rates. A coordinated swarm of devices/multi-level pathogen mitigation devices can be provided based on a number of people and associations between disinfection devices. That is, the dynamic treatment system can include a coordinated swarm of pathogen mitigation devices. A cloud-based system, AI software, and medical diagnostic machine learning can be utilized to analyze the data obtained from the swarming devices. The swarm coordination of HVAC, portable treatment devices, surface treatment devices, integrated treatment devices, air treatment devices and systems can enhance performance beyond the individual controlled performance.

Engineered controls for pathogen reduction can be provided in building controls. For example, a face recognition camera, AI software to collect/analyze data can enable a number of global control decisions. The design and method of creating mitigation devices that have multiple levels of performance that can be controlled as a global control system. Sensor systems within mitigation devices that enable localized control decisions but collectively the sensor data enables global control decisions that can further improve local and zonal performance.

Pathogen reduction device associations can be accomplished in a variety of different ways. One strategy for pathogen reduction device association may be network-based, where all devices communicate to a central server, which can be located locally or in the cloud. A spatial relationship between the pathogen reduction devices or between each pathogen reduction device and a shared environment map can be utilized to ascertain device location, which can be utilized to push settings to devices located within a threshold distance to a loaded area. The settings can be weighted based on distances such that devices that are further away from the loading trigger dictating heightened pathogen reduction receiving less-drastic setting changes.

In alternative embodiments, the pathogen reduction devices are not necessarily connected to a central server, but rather configured to communicate wirelessly to devices within a certain range. For example, each pathogen reduction device may include a Bluetooth adapter and be configured to communicate using a BLE mesh and self-locating units that broadcast 'load levels' that other devices nearby can react to. Devices that know about high loading can broadcast that information, and devices that receive the message can react accordingly, with the reaction of devices being reduced the further away from the source of transmission such that they react less drastically to the loading indication. By monitoring the BTLE SSID signal strength the control system can be configured to act according to general proximity by signal strength as one level of proximity understanding. Another layer is the pressures and timing related to physical adjacencies. A room below will not have both but may have a good signal for example. A mesh network can tie these systems together for a more advanced understanding of proximity. Floor levels may be a configurable setting that assists the adjacent information and formation of the mesh and adjacent understanding.

Figure 8:
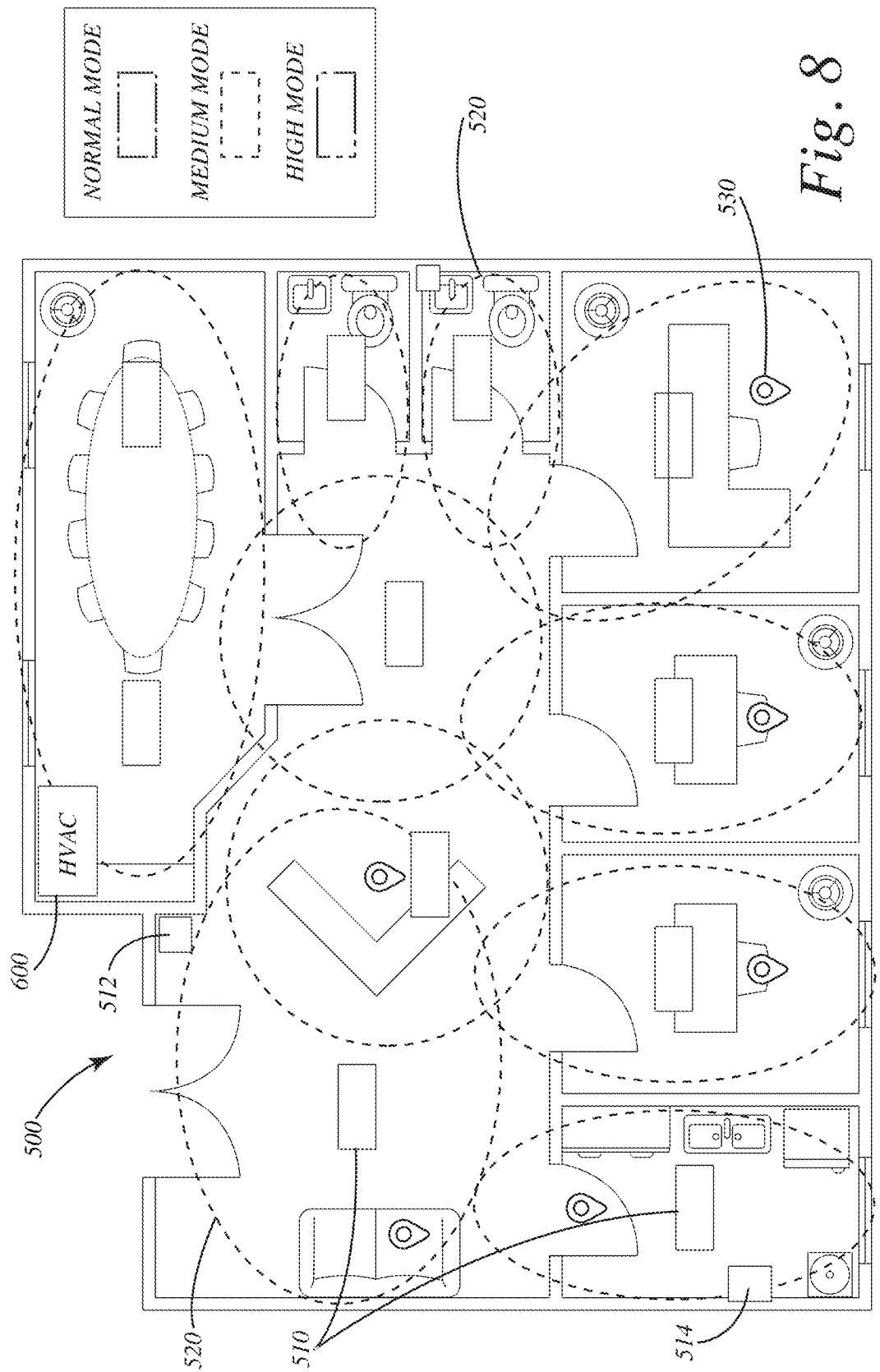
FIG. 8 illustrate a visual representation of operation of various pathogen reduction devices within a dynamic air treatment system according to a fourth exemplary scenario.

Referring to FIG. 8, it shows an alternative building level response for the dynamic treatment system. In this embodiment, the dynamic treatment system coordinates with a heating, ventilation, and air conditioning ("HVAC") system 600. The building level control can respond to HVAC changes to help clean the air and surfaces throughout the space.

The pathogen reduction device cleaning response can vary depending on the loading. For example, UV-C disinfection devices disposed at workstations can monitor interactions and inform the cleaning response. Further, the average cleaning cycle completion percentages can factor into determining a load per location. Workstation interactions at these workstation disinfection devices generally occur when people are present, and therefore are a meaningful indicator of human activity. Spikes in such activity provide a relatively easy way to understand when areas are loaded, without additional hardware.

The dynamic treatment system can be configured to associate nearby units in a variety of different ways. Two exemplary strategies are explained below, but in alternative embodiments other strategies can be utilized.

The dynamic treatment system logic can be cloud-based, with settings pushed to all devices known to be located 'nearby' the loaded area with those further away receiving less-drastic setting changes. When configuring a building, the floor plan can be used to associate device ID's (pathogen reduction devices, sensors, or other system devices) to specific or general locations (e.g., by room, or location on a floor map representation of a room) when possible. During installation and set-up, these associations can be configured via a mobile device application, or via communication with a cloud application. Different dynamic treatment systems can have different network configurations. In some configurations, a mesh network is utilized to build a cluster identifier list by room for the system, e.g., utilizing signal strength clusters that associate groupings of devices within the mesh. For each room, associations can be made for each door, window, elevator, stairway, HVAC grouping, commons areas and restrooms. Accordingly, by associating a pathogen reduction device, sensor, or other device with a particular room, an association is also created with the various characteristics of that room (e.g., door, window, elevator, stairway, HVAC grouping, commons areas, and restrooms).

The logic could also be offline, device-based with a BLE mesh and self-locating units that broadcast 'load levels' that other devices nearby can react to. Devices that know about high loading can broadcast that, and as devices get further and further away from that source, they react less drastically.

HVAC pre and post pathogen reduction mitigation. In homes and areas when HVAC changes or cycles, we can see post cycle or change mitigation measures. The response profile in these cases may be both air treatment rates and surface treatment after some measured settling time. The settling time will be related to air flow and turbulence in that space.

Figure 9:
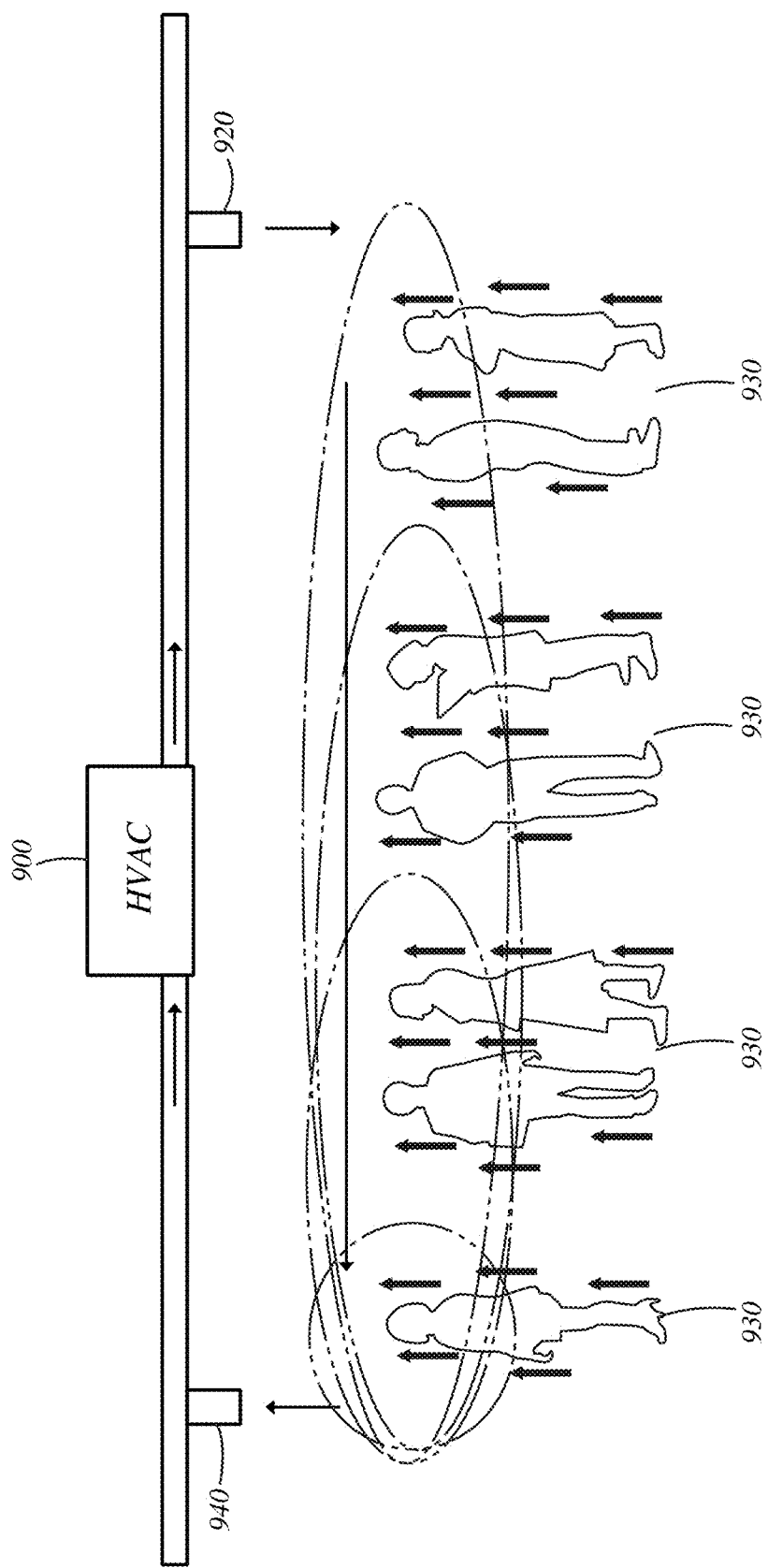
FIG. 9 illustrates an exemplary particulate flow in an open indoor environment caused by human thermals, human breathing, and HVAC outlets and return vents.
Figure 10:
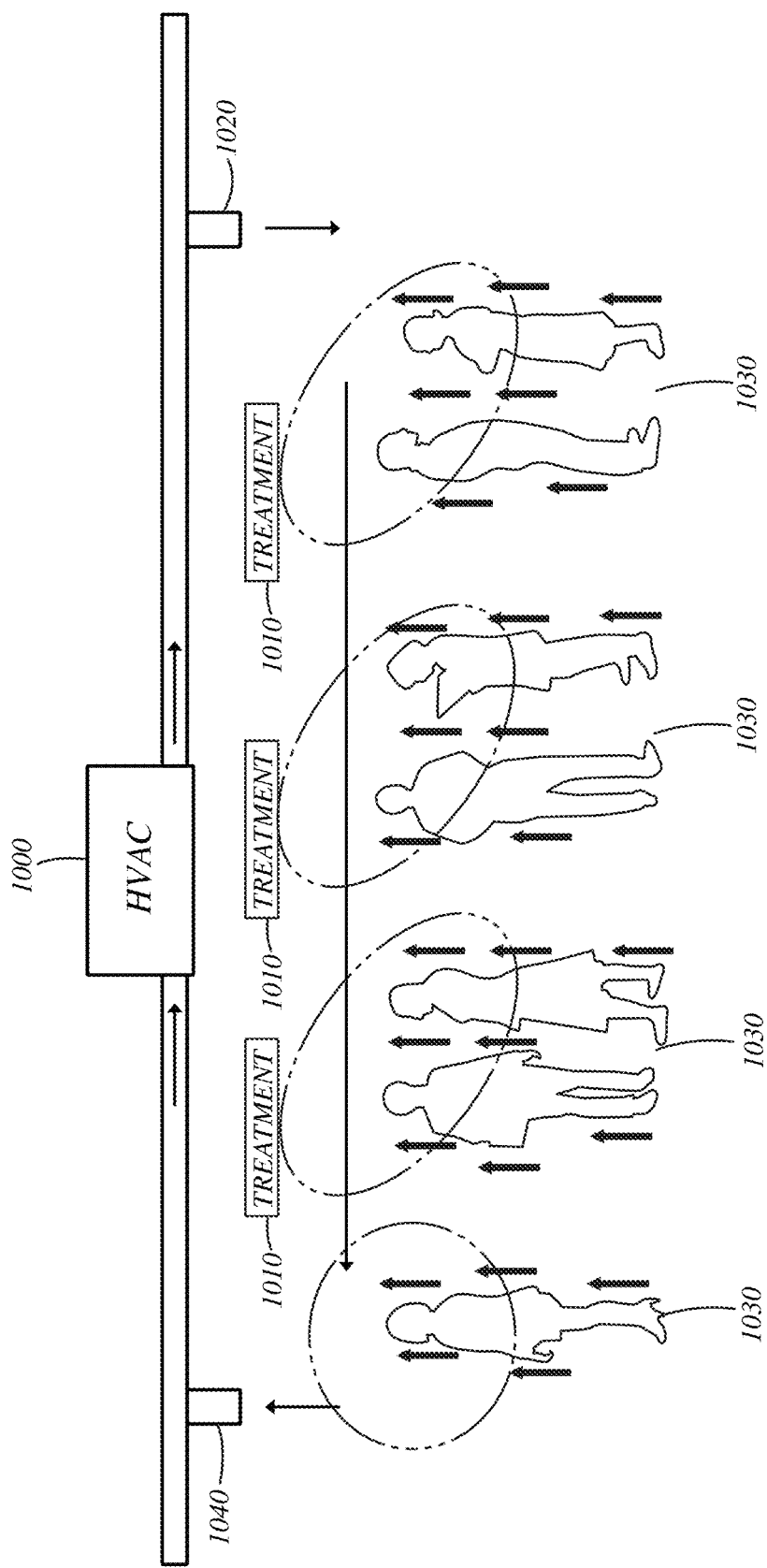
FIG. 10 illustrates one embodiment of a dynamic treatment system configuration with a plurality of pathogen reduction devices configured to disrupt particulate flow and treat pathogens in the open indoor environment of FIG. 9.
Figure 11:
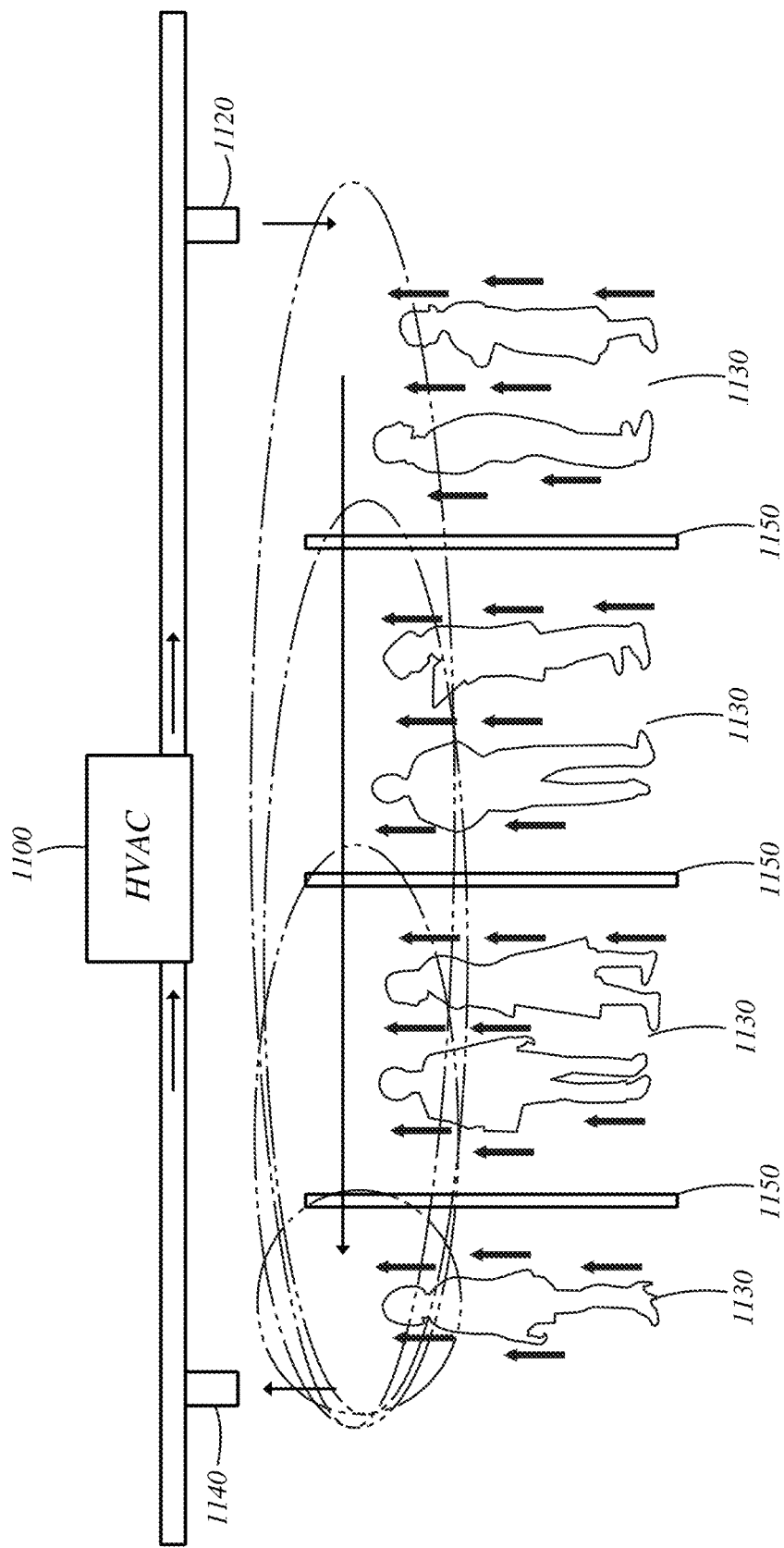
FIG. 11 illustrates an exemplary particulate flow in a compartmentalized indoor environment caused by human thermals, human breathing, and HVAC outlets and return vents.
Figure 12:
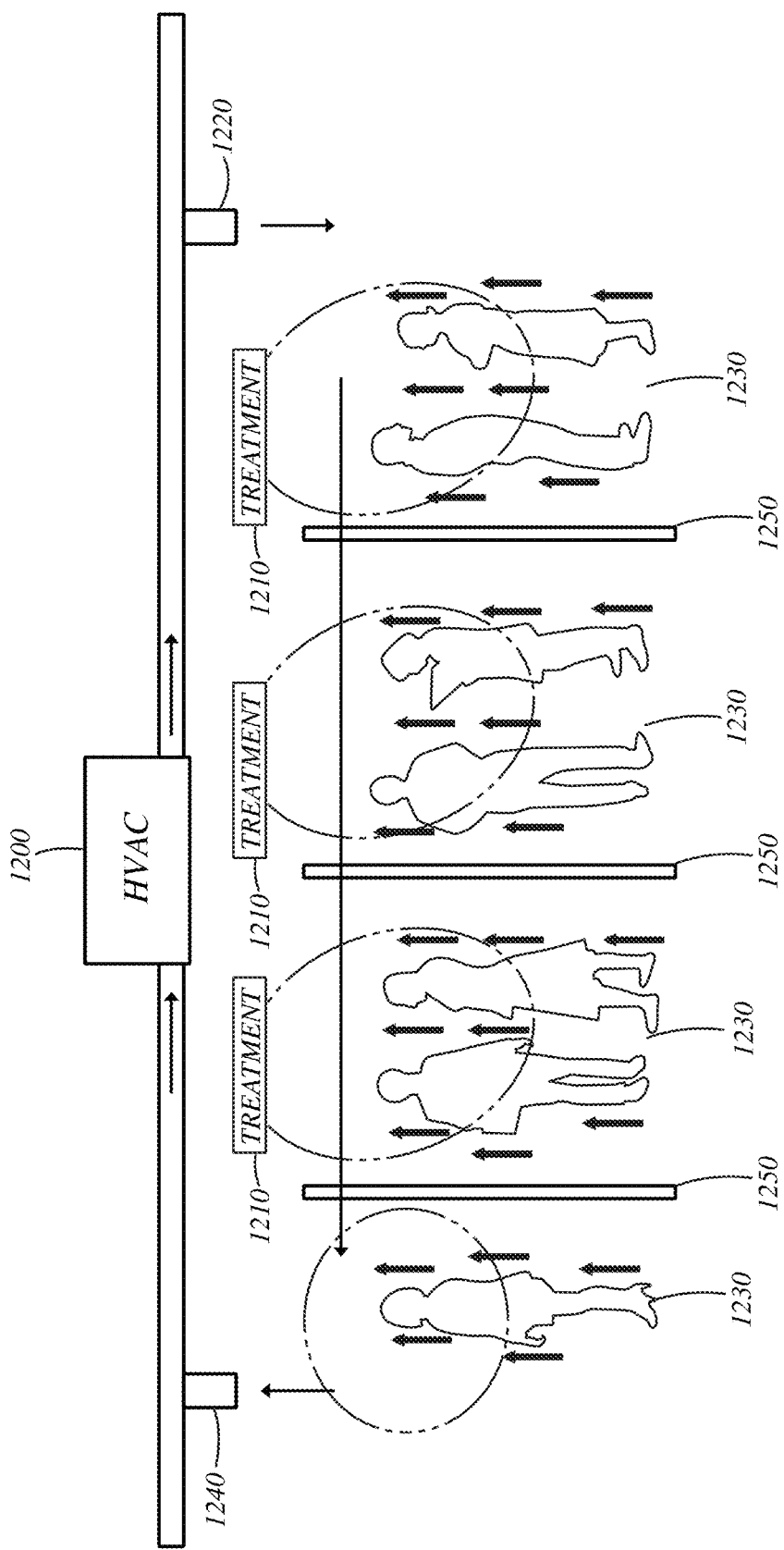
FIG. 12 illustrates one embodiment of a dynamic treatment system configuration with a plurality of pathogen reduction devices configured to disrupt particulate flow and treat pathogens in the compartmentalized indoor environment of FIG. 11.
Figure 13B:
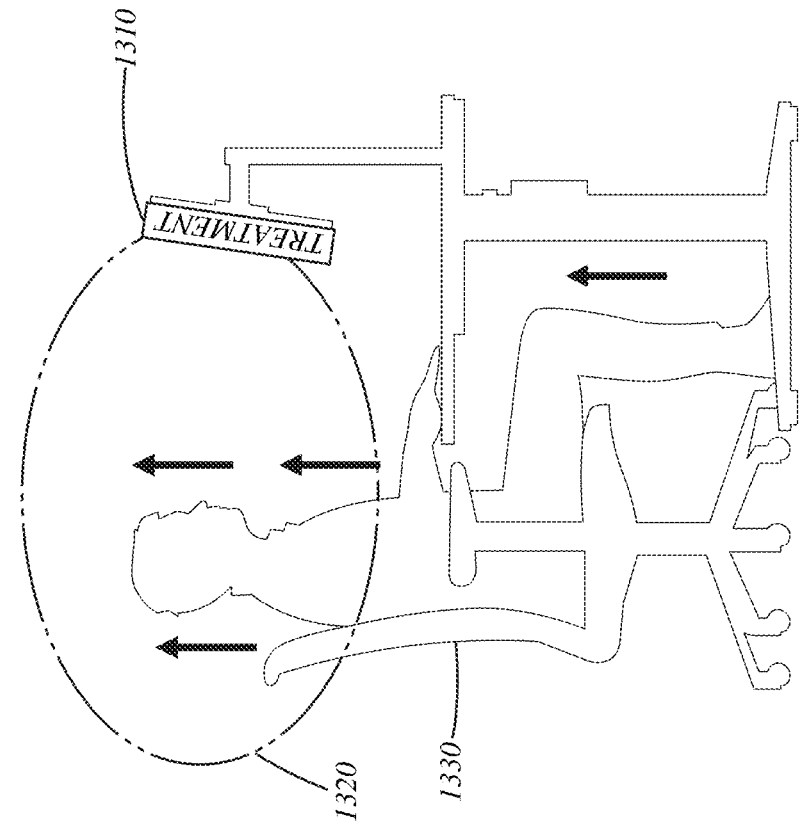
FIGS. 13A-B illustrate two pathogen reduction device configurations for a sitting position at a desk.
Figure 13A:
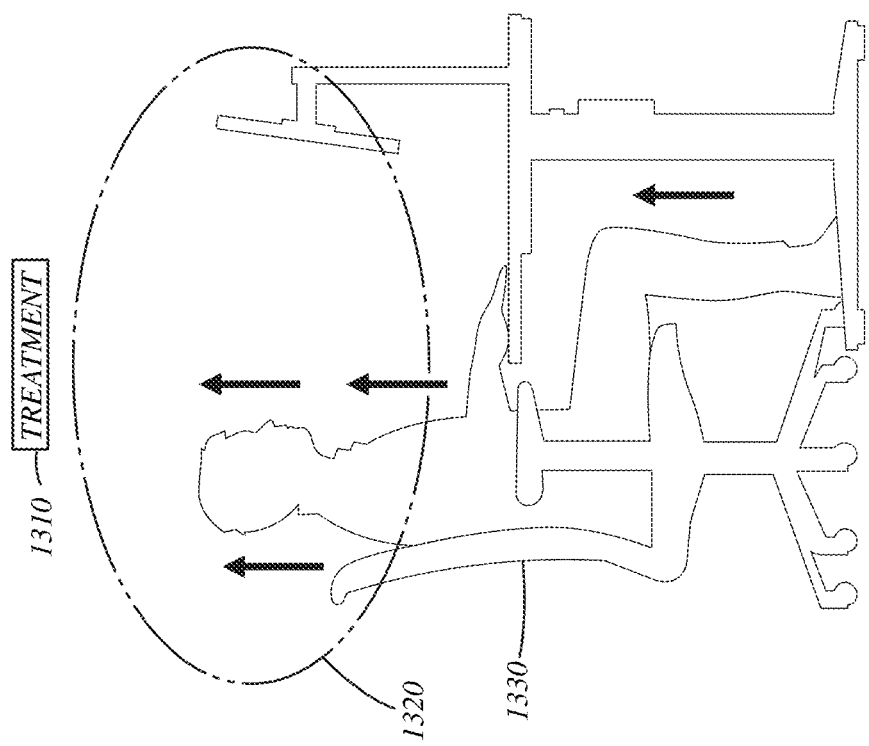

Dynamic Air Treatment Systems Above Airflow. FIG. 9 illustrates the representative airflow in a space containing an HVAC 900 in accordance with one embodiment. Particulates from the breath of groups of people 930 flow through the room as the HVAC 900 moves the air from the outlet 920 to the return 940. The thermal rise of each individual within the room along with breathing is carried across the breathing zones of others.

FIG. 10 illustrates how a dynamic treatment system including dynamic air treatment systems 1010 influence the airflow depicted in FIG. 9. The dynamic air treatment systems 1010 intercept the air streams from the individuals and break the potential chain of infection within the HVAC 1000 stream. The air treatment dosage (including speed) can be controlled in such a manner to be proportionate to the occupancy or loading levels associated with the location of each individual dynamic air treatment system 1010. The device level pathogen reduction protocol can be configured with minimum and maximum treatment levels and can be configured specifically for building and zone level occupancy expectation information. Because room temperature is generally cooler than human body temperature, human breath will tend to ascend toward the ceiling, as indicated in FIGS. 9-11 by the arrows pointing toward the ceiling. This air flow path in combination with other factors, such as the building/room layout can inform the positioning of pathogen reduction devices within the system to enhance harvesting of the human expelled air in a zonal fashion, not at the edges of the room but throughout. By monitoring carbon dioxide ($CO_2$) levels within a room or within a particular area, occupancy information can quantify to verify, enhance, or replace occupancy sensor data obtained in other ways. In this way, the system can self-manage maintenance and energy costs over time by dynamically responding. The system can be configured to account for various costs and considerations by exchanging information over a network connection to the Internet to a remote server. This can include providing and receiving information about lamp and LED life, filter life, sensor life, etc. The article entitled "Mathematical models for assessing the role of airflow on the risk of airborne infection in hospital wards" by Noakes and Sleigh, which can be accessed at https://www.ncbi.nlm.nih.gov/pmc/articles/PMC2843948/discusses how an HVAC can act as a transport for pathogens and infection.

Zone level pathogen interception. Dynamic treatment systems in accordance with the present disclosure can intercept or limit pathogens from migrating past a certain point. Systems that create airflow, such as an HVAC system, may transport pathogens along an airflow path and inadvertently expose human beings over the distance of the airflow. This can cause movement of pathogens from places such as outside of operating rooms, bathrooms, hallways, common areas to other areas, which perhaps are less expected to have a high pathogen level. The interception of these streams of pathogens within the targeted breathing zones becomes an opportunity to break the chain of infection.

FIG. 11 shows an exemplary flow of particulates from people 1130 through normal breathing within an environment with an active HVAC system 1100. In this depicted representation, for exemplary purposes, the HVAC 1100 generally causes air to move from an outlet 1120 to a return 1140. Although there may be walls 1150 or another form of partition between the groups of people 1130, the particulates from each group 1130 may still flow between the groups 1130, for example through vents in the walls 1150. This is a common occurrence in many different types of environments, including cruise ship cabins and office buildings.

Pathogen stream, air flow management. FIG. 12 shows the embodiment of FIG. 11 further including at least one dynamic air treatment system 1210. As depicted, the air within zones of the groups of people 1230 may be intercepted and treated locally by the at least one dynamic air treatment system 1210. This may mitigate the contaminating opportunity of the air flow. This zonal level of air treatment enables the microdroplets and air treatment to be intercepted and treated at the source for source control.

FIGS. 13*a*-13*b* show dynamic air treatment systems 1310 installed for a sitting position. In FIG. 13*a*, a dynamic air treatment system 1310 is installed above the seating position of a person 1330. The particulates 1320 the person 1330 breathes out travel upward and are treated by the dynamic air treatment 1310 system before the air is recirculated into the room. In FIG. 13*b*, a dynamic air treatment system 1310 is installed at the level of the person's 1330 computer monitor. The particulates 1420 the person breathes out travel upward and are treated at the level of the person's 1330 computer monitor as the air is recirculated into the room. In one embodiment, the dynamic air treatment system 1310 is mounted to the person's 1330 computer monitor.

The breathing trajectory makes this a personal system for treating your local air. Surface system can also be utilized for surfaces and keyboards. The table may have a downdraft air treatment system build into the table, the white board, office panel or tack board may have an air treatment system built into the surface with area facing the user being the function surface and behind we are treating air.

Portable Dynamic Air Treatment Systems. FIG. 14 shows an arrangement of portable dynamic air treatment systems 1400 in a residence according to one embodiment. The portable dynamic air treatment systems 1410 may alternatively be referred to as a portable home system. Portable dynamic air treatment systems 1410 may also be managed by load monitoring and environmental monitoring. Each portable dynamic treatment system 1410 may have a treatment zone 1420. In one example, the arrangement of dynamic air treatment systems 1400 may be referred to as a portable coordinated home. The automated engineered control system would change based on loading, cleaning, HVAC cycles, vacuuming, movement, people count etc. Note multiple systems to manage flow and segment interception areas. If grandpa and grandma are home the treatment devices may be on low, when the grand kids visit the occupancy monitors trigger activity and step up the speed of treatment.

Portable air treatment units. Portable air treatment units can be configured for adjustable height tailored for different breathing zones. The portable units can be configured with multiple performance levels that influence a wide change in pathogen load. The units can accommodate multiple breathing zones at different heights. Further, the portable air treatment units can have an oscillating aspect such that they can be configured as oscillating air treatment units that can clean the surrounding area where a person is sitting.

FIG. 15 depicts an arrangement of portable dynamic air treatment systems 1500 for a non-residential environment according to one embodiment. These portable dynamic air treatment systems 1510 may also be managed by load monitoring and environmental monitoring. The dynamic air treatment systems 1510 may alternatively be referred to as portable commercial systems. Each portable dynamic air treatment system 1510 may have a treatment zone 1520. In one embodiment, the non-residential environment is a commercial environment. In one example, the arrangement of dynamic air treatment systems 1500 may be referred to as a portable coordinated commercial system. The automated engineered control system would change based on loading, cleaning, HVAC cycles, vacuuming/physical cleaning, movement, people count etc. Note multiple systems to manage flow and segment interception areas.

FIG. 16 shows a portable dynamic air treatment system 1610 for use with a person 1630 in a standing position. The portable dynamic air treatment system 1610 may be telescoping, and may be either manually adjustable, automatically adjustable, or a combination of manual and automatic adjustment. In one embodiment, the tube can be either manually telescoping or driven by particulate sensing and sampling for optimum setting for maximum effect. The system may be referred to as a standing unit. The portable dynamic air treatment system may be designed for the breathing zone of a standing person. The portable dynamic air treatment system may have a breathing zone 1620 and an exhaust zone 1640.

FIG. 17 shows a portable dynamic air treatment system 1710 for use with a person 1730 in a sitting position. The system 1710 may be referred to as a sitting unit. The portable dynamic air treatment system 1710 may be telescoping, and may be either manually adjustable, automatically adjustable, or a combination of manual and automatic adjustment. The portable dynamic air treatment system 1710 may have a breathing zone 1720 and an exhaust zone 1740. The height of the breathing zone 1720 may be adjusted to match the sitting height of a person 1730. Alternatively, or additionally, the sitting height of a person 1730 may be adjusted to match the height of the breathing zone 1720 of the portable dynamic air treatment system 1710.

Specific Dynamic Air Treatment Systems Examples. FIG. 18 depicts a hospital bed 1800 with a dynamic air treatment system 1810 according to one embodiment. The dynamic air treatment system 1810 may be designed for the breathing zone of a patient. The system may be battery powered and charged wirelessly or otherwise. The system may function when moving down the hallway and in the room. The rails may be used as the inlet vents for pulling the air away from the patient. The air may encounter the dynamic air treatment system 1810 and then the system 1810 may release the treated air into the room. The air curtain pulls air from and away from the patient. The air curtain may be incorporated into beds and chairs.

Air curtain for a hospital bed. The air curtain hospital bed has a battery powered and wirelessly charged air treatment system that pulls air away from the patient. This protects both the patient and the health care staff. Not only in the room but also in the hallways and potentially even on gurneys in the ambulance. The air is drawn from a point within the breathing zone, treated and exited. It would use a filter and UV and/or non thermal plasma to deactivate any pathogens. The air curtain can be incorporated into the bed rails or a structure about the patient's head and breathing zone.

Plasma and UVC Treatment Zones. Non-thermal plasma devices may be incorporated as pathogen reduction devices into a dynamic treatment system of the present disclosure to provide pathogen reduction. For example, a packed plasma bed can be utilized to deactivate pathogens, which provides a reliable method to treat specific use cases. UV and non-thermal plasma may both be used in conjunction.

Application specific air treatment systems. Transport Related Pathogen mitigation can be provided for various applications. For example, devices and systems can be configured to mitigate or otherwise reduce pathogens in specific environments relating to airlines, busses, subways, automobiles, or other passenger vehicle cabins. Various application specific air treatment systems can be integrated into a dynamic treatment system of the present disclosure. For example, an air treatment system configured for use in a passenger vehicle cabin of a plane, train, or automobile can assist in providing effective and efficient pathogen reduction.

Many vehicles have airflow systems and vents associated with individual passenger seating. Airflow through these vents is generally configured to be in a direction toward the passenger, which is opposite of the desired flow from a pathogen reduction and containment standpoint. For pathogen reduction and containment, these vents should be configured to intake passenger breath and the plume of air surrounding the passengers. Instead, by blowing air outwardly through these vents, they tend to scatter the air and pathogens being carried upward by that airflow and scatter it downward and around toward surrounding passengers. By reversing the direction of airflow and configuring these vents as intakes, the spread of pathogens can be reduced significantly. Further, a treatment system can be integrated that treats the air before returning it back to the cabin. The same process can be applied in other passenger vehicles, such as for automotive air treatment.

FIG. 19 shows a representative scene of a dynamic air treatment system 1910 installed in a passenger vehicle according to one embodiment. For example, the passenger vehicle may be an airplane or a train. The dynamic air treatment system 1910 intercepts airflow between passengers to help prevent pathogen impact to other passengers. For example, as the passengers 1930 breathe, particulates they expel travel upward due to the thermodynamic nature of human breath in a cooler room or compartment. The dynamic air treatment system 1910 installed in the roof above the passenger area treats the air in the passenger area where it naturally moves, harvesting that breath trajectory.

The treated air may then be cycled back into the vehicle cabin. In this way, the particulates from one passenger 1930 or from attendants 1930 may not infect the other people 1930 in the vehicle cabin. Additional air blade concepts can be used to draw air away from the breathing zone to limit surrounding impact. The present system mixes and shares the air you exhale with others rather than harvesting and treating that air as we show here. The treatment may be HEPA or UVC. It may also be both.

Figure 20:
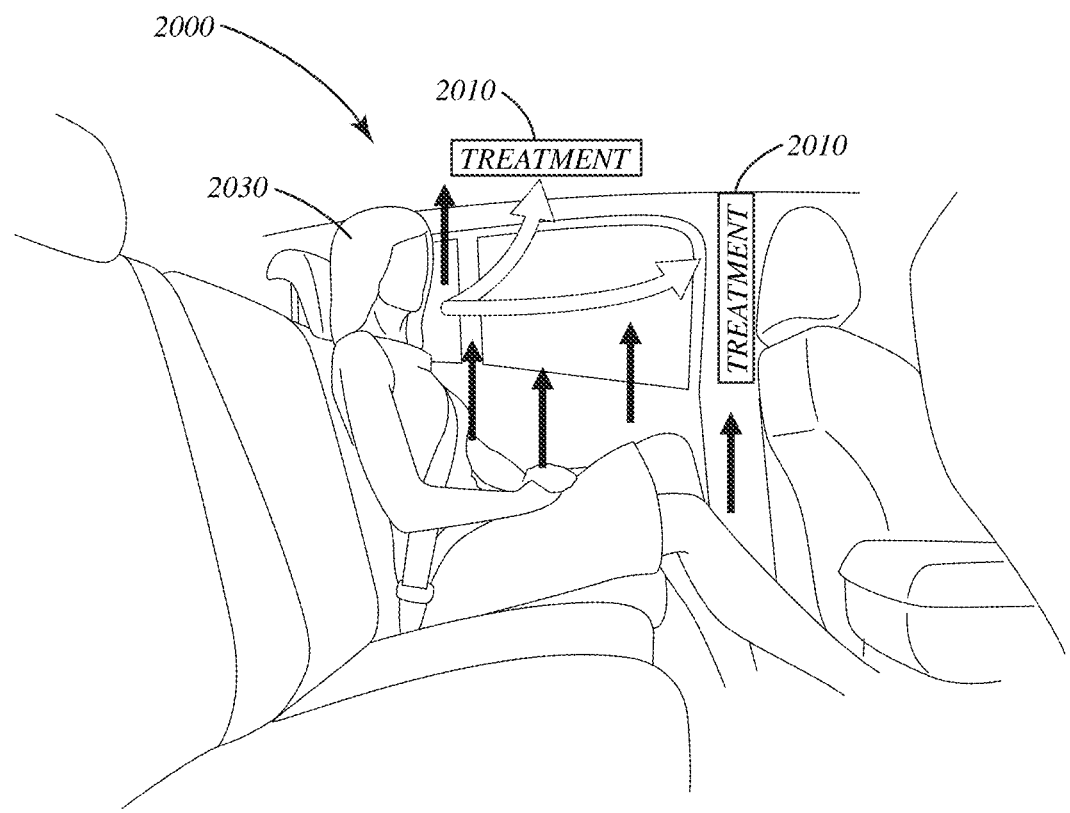
FIG. 20 shows another exemplary pathogen reduction device installed within a vehicle cabin.

FIG. 20 shows an example of an arrangement of dynamic air treatment systems 2000 installed in an automotive cabin according to one embodiment. A dynamic air treatment system 2010 may be designed for the breathing zone of an automotive cabin. In one embodiment, the automotive may contain a dynamic air treatment system 2010 installed above a passenger 2030 and a dynamic air treatment system 2010 installed in front of a passenger. The dynamic air treatment system 2010 installed above a passenger 2030 may be mounted on the ceiling of the vehicle or on the wall of a vehicle above the breathing height of the passenger 2030. In alternative embodiments, the automotive may only contain a dynamic air treatment system 2010 installed above a passenger 2030, only a dynamic air treatment system 2010 installed in front of a passenger 2030, or a plurality of dynamic air treatment systems 2010 mounted throughout the automotive cabin in various positions, not limited to above and in front of a passenger 2030. The dynamic air treatment systems 2010 may be mounted in the automotive cabin by any suitable means.

The dynamic air treatment systems 2010 may capture and isolate the air exhaled by each person within the cabin 2030. The treated air may then be recycled back into the cabin. Capturing and treating the air can allow the air from each person 2030 to be better isolated to that person which may result in a healthier vehicle cabin. The dynamic air treatment systems 2010 may have the same multi-level performance and dynamic loading response as described above with respect to other embodiments.

Elevator Pathogen Mitigation. Elevator carriages generally involve multiple passengers in a physically confined space forcing the sharing of air supply. Accordingly, elevators can be a significant source of pathogen spread among people in a building environment. A pathogen reduction device can be installed in an elevator to mitigate pathogen spread in an elevator environment. In one embodiment in accordance with the present disclosure, an airflow system is controls airflow within the elevator carriage. Specifically, air is configured to flow through the holes in the elevator platform that passengers stand on during elevator travel. More specifically, the airflow system is configured to cause air to flow from the bottom of the elevator to the ceiling of the elevator carriage in multiple segmented laminar sections. These segmented laminar sections do not mix in a significant manner. That is, as passengers' breath normally during the elevator ride, their inhaling and exhaling of air does not significantly impact or disturb the laminar flow of air from the floor of the elevator to the ceiling. Put another way, the laminar flows of air streams act as air curtains between people standing on the elevator platform. This is significantly less burdensome than plexiglass or other physical separators, which have been considered to prevent sharing of air among elevator passengers. The air flow system can work in conjunction with an air treatment system that can either expel or recycle the air.

Figure 21A:
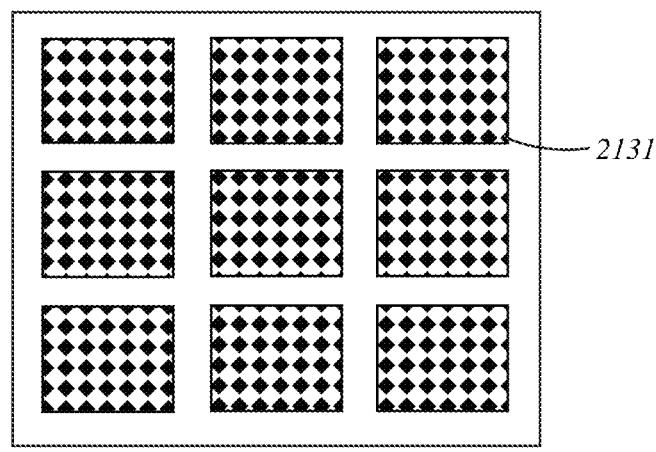
FIGS. 21A-C show several views of a dynamic treatment system configured for an elevator according to one embodiment of the present disclosure.
Figure 21B:
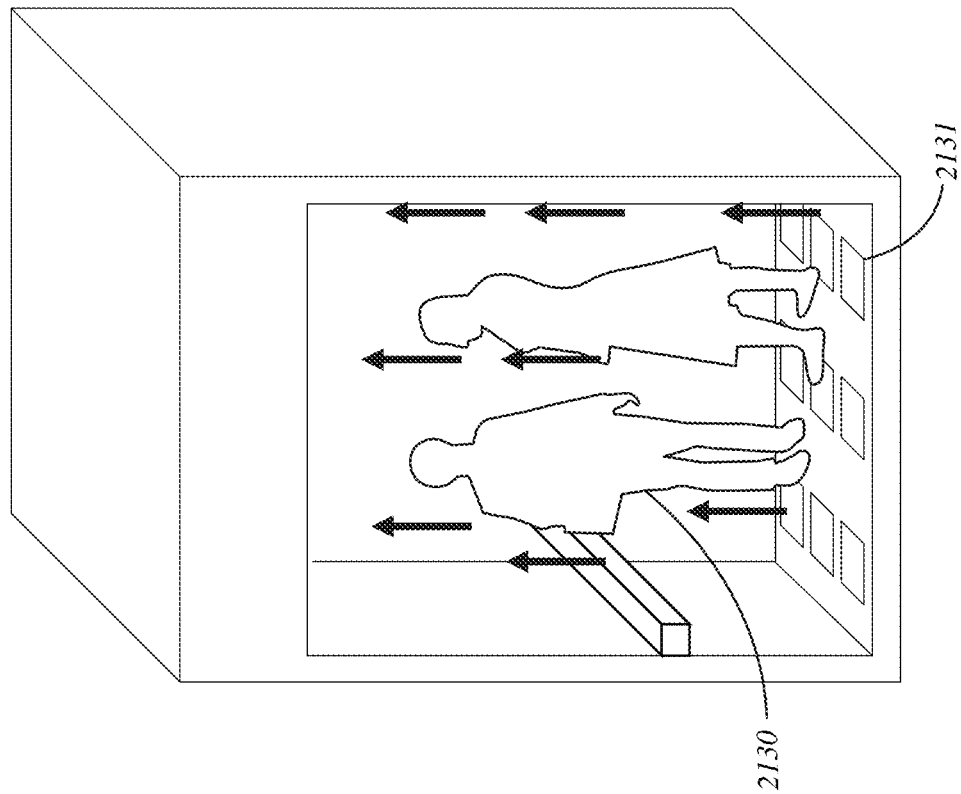
Figure 21C:
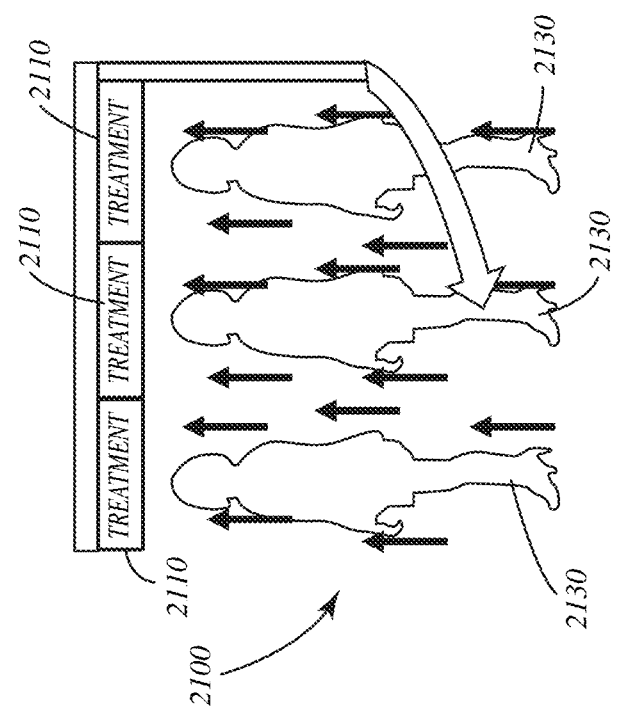

FIGS. 21A-C show an exemplary elevator with such a configuration. Specifically, the elevator includes a plurality of air flow systems or air treatment systems 2100 configured as discussed above to generate laminar airflow from the floor to the ceiling of the elevator. The arrangement of air treatment systems 2100 segment air among a plurality of different sections in the elevator where a different person 2130 can stand on the elevator platform. In the depicted embodiment, the configuration and arrangement provide nine distinct zones, but in other embodiments additional or fewer zones can be provided. The arrangement and configuration of the air treatment systems 2100 facilitate air movement to segment air into laminar flow. Devices to create laminar airflow are well-known and therefore the details and specifics are not being described in detail. One arrangement of such laminar airflow devices is depicted in FIGS. 21A-C. This ultimately provides a healthier way for multiple passengers to occupy a close physical space, such as in an elevator. Although this embodiment is described within the context of an elevator carriage, a similar laminar airflow curtain arrangement can be generated utilizing multiple air treatment systems as shown in other capacities and applications. The arrangement of air treatment systems 2100 cabin generates multiple streams of laminar airflow from the bottom of the elevator platform. Alternatively, the laminar airflow can be generated mid-compartment to a ceiling air collector, aiming to prevent or reduce contact with multiple people 2130, and limiting air exposure to each person, respectively.

The elevator can include a one or more overhead vents and floor vents to facilitate the laminar airflow paths/curtains. Although a matrix of holes is depicted in FIG. 21A to essentially form nine distinct vents 2131, each in fluid communication with an air treatment system that can generate the laminar airflow in the defined airflow path (i.e., through the sidewalls of the elevator carriage), in other embodiments, a series of slits can be utilized instead. Because the air is treated toward the ceiling in the depicted embodiment, the return path to the floor (or mid-way point of the carriage) can be a shared path because the air is all treated together). The ceiling of an elevator can also provide an LED lighting opportunity, i.e., LEDs can be installed along the vents or the spaces between the vents 2131. There may be individual overhead vents for each position of a person in an elevator, which can also help to separate and define visually the laminar airflow paths for passengers. In some embodiments, separate return air paths can be provided such that each airflow path is separated from one another. FIG. 21B shows the airflow from floor inlet vents. FIG. 21c shows an arrangement of dynamic air treatment systems 2110 installed in the ceiling of an elevator. As depicted, one dynamic air treatment system is installed above each passenger 2130 or user in an elevator. As each passenger 2130 breathes, their particulates travel upwards. The particulates encounter the air treatment systems 2110 and the air is recycled back into the elevator. As depicted, the air can travel from the air treatment systems 2110 through the sidewall of the elevator (or through an air path provided by a tube or other conduit) to a position lower than the breathing zone of the passengers of the elevator (e.g., about midway down the elevator carriage or via floor vents 2131 of the elevator platform. In an alternative embodiment. The air travels to the from the treatment systems through the vents and elevator air transport system to re-enter the elevator—or if the air is discharged, a fresh air source or treated air source can be utilized to supply the elevator instead of routing treated air back to the elevator cabin. In yet another embodiment, the air treatment systems 2110 may be installed in the floor of the elevator in addition, or instead of near the elevator cabin ceiling. The air can travel upward and be recycled through the body of the elevator to the dynamic air treatment systems in the floor. The air may then be treated and allowed to re-enter the body of the elevator. In another embodiment, the dynamic air treatment systems 2110 may be installed in both the floor and the ceiling of the elevator.

Figure 22:
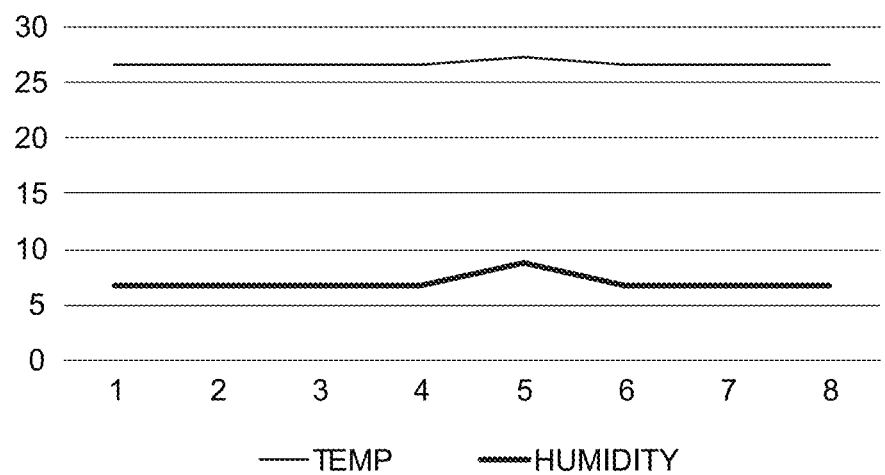
FIG. 22 shows an exemplary graph of a human breath signature based on humidity level and ambient temperature level.

Triggering the Dynamic Air Treatment System. FIG. 22 shows an example of a heat signature of human breath. Micro temperature sensing of heat signatures can be performed by the system. As depicted, small increases in temperature and humidity as a person breathes can be detected by the system. The humidity and micro temperature climate can be measured to determine the loading of a dynamic air treatment system.

Humidity sensing and temperature rise monitoring. One aspect of body generated pathogens is that initially body heat can assist in the transfer or movement of these particles. The natural local humidity for some of these systems can be easily monitored. Automotive, train and plan cabins can easily detect humidity locally as a product of breath. For example, in a vehicle local seating positions can be monitored, and treatment can be load specific. The temperature of the exhaled breath is better understood with each passing day as it relates to the map of human physiology and disease.

The average human releases 400 Btu per hour (400 fully burned wooden matches as base layman's example) at rest, more if they are moving around (dancing, involved in a show etc.) The system can be configured to trigger based on this formula. That is, the system can be configured to take the Btu total load and measure it against the R value of the building envelope. The temperature of a healthy human being is about 37 degrees Celsius, while the exhaled breath temperature varies around 34 degrees Celsius. This difference can be detected and acted upon, e.g., by elevating the treatment level in a variety of different ways, such as, but not limited to, those discussed above.

Figure 23:
FIG. 23 shows a forward-looking infrared ("FLIR") heat signature within a room.
Figure 24:
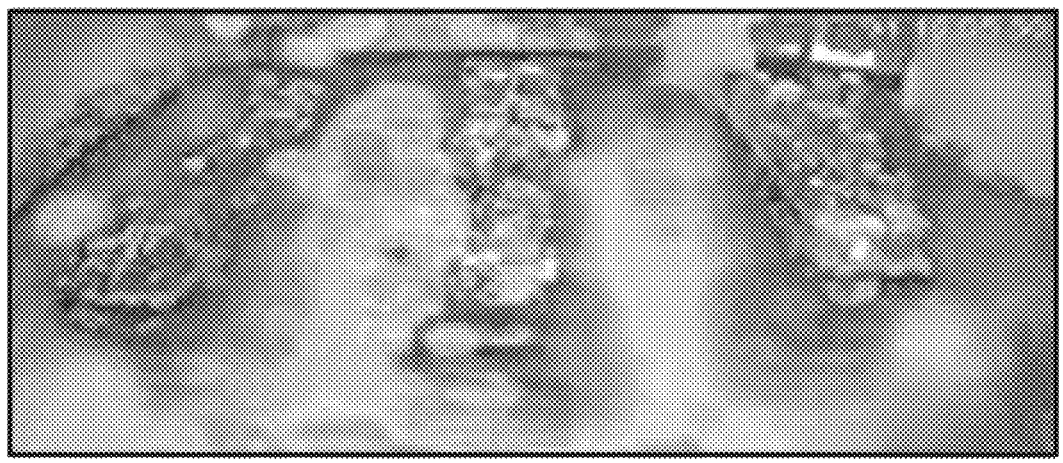
FIG. 24 shows a mm wave radar tracking heat map of movement.
Figure 25:
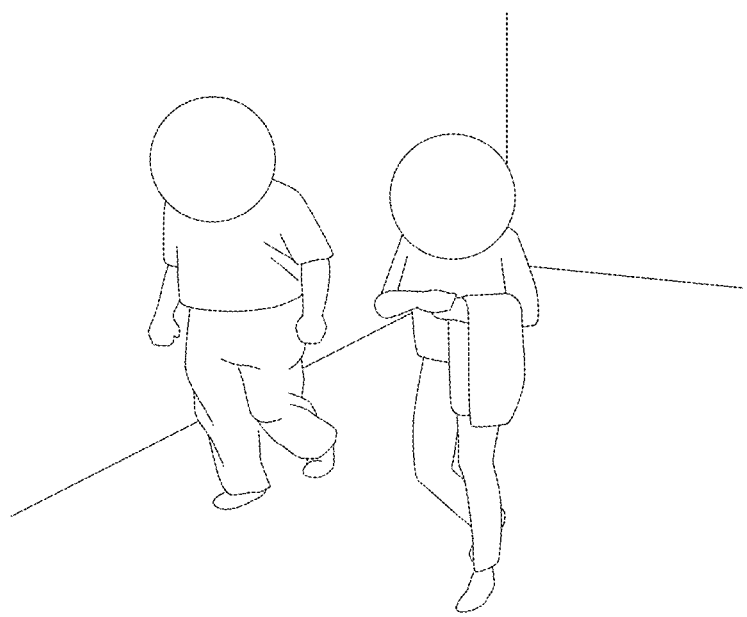
FIG. 25 shows a mm wave radar tracking heat map configured for people counting.

FIG. 23 shows an image from a sensor that can be incorporated into the dynamic treatment system. Specifically, the image of FIG. 23 is a forward-looking infrared ("FLIR") heat signature within a room captured by a FLIR camera. FLIR can be used for image recognition and heat signatures. In one embodiment, FLIR may be used for people counting. The FLIR signature of a room can be used for driving the building level feedback. FIGS. 24 and 25 show a mm wave radar tracking heat maps of movement and people according to one embodiment. The heat maps depicted can be created using radar imaging. These sensors can be integrated into dynamic treatment systems in accordance with the present disclosure.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A pathogen reduction control system for a building, the system comprising:
   a coordinating controller configured to:
      receive sensor information from one or more sensors distributed throughout the building, the sensor information including one or more of occupancy information, heat information, pressure information, air quality information, or humidity information;
      identify biological loading levels throughout the building based on the received sensor information; and
      transmit override pathogen reduction device instructions based on the identified biological loading levels; and
   a plurality of pathogen reduction devices disposed throughout the building, each pathogen reduction device including a UV source, a communication interface a controller, and memory, each pathogen reduction device being configured to either:
      reduce pathogens by operating according to baseline instructions stored locally in memory and without influence from the coordinating controller, wherein the baseline instructions control operation of the pathogen reduction device based on one or more associated sensors providing one or more of timing information, touch information, infrared information, motion information, accelerometer information, or temperature information, or
      reduce pathogens by operating based on override pathogen reduction device instructions received from the coordinating controller;
   whereby the coordinating controller and two or more of the plurality of pathogen reduction devices cooperate to provide coordinated pathogen reduction based on the biological loading levels throughout the building.

2. The pathogen reduction control system of claim 1 wherein the sensor information from the one or more sensors distributed throughout the building includes pressure information associated with different rooms of the building connected by air passage;
   wherein the coordinating controller is configured to identify biological loading levels by identifying a pressure differential between different rooms of the building via the pressure information; and
   wherein the coordinating controller is configured to transmit override instructions to one or more of the plurality of pathogen reduction devices based on the pressure differential identified by the coordinating controller.

3. The pathogen reduction control system of claim 1 wherein the coordinating controller is configured to execute proportional pathogen risk management commands based on an expected impact of biological load.

4. The pathogen reduction control system of claim 1 wherein the coordinating controller is configured to calculate a chain of pathogen risk management assessments based on a tree relationship between rooms of the building, wherein the calculations include proportional impact based on airflow path and biological load of each room.

5. The pathogen reduction control system of claim 1 wherein the coordinating controller is configured to identify a biological load of a first room based on a combination of the sensor information from one or more sensors associated with the first room and sensor information from one or more sensors associated with one or more adjacent rooms.

6. The pathogen reduction control system of claim 1 wherein the coordinating controller is configured to transmit the override instructions based on an expected or estimated biological load change.

7. The pathogen reduction control system of claim 1 including wherein the plurality of pathogen reduction devices disposed throughout the building include multiple sets of pathogen reduction devices disposed throughout different zones within the building, and wherein the coordinating controller is a local controller associated with one of the different zones within the building that is configured to transmit override instructions to the set of pathogen reduction devices disposed in that associated zone.

8. The pathogen reduction control system of claim 1 wherein the coordinating controller is configured to transmit override instructions to one or more of the plurality of pathogen reduction devices to adjust one or more of UV bulb intensity, dose time, and delay time.

9. The pathogen reduction control system of claim 1 wherein the coordinating controller is configured to transmit override instructions to adjust HVAC airflow.

10. The pathogen reduction control system of claim 1 wherein the coordinating controller is configured to transmit override instructions to one or more of the plurality of pathogen reduction devices to adjust operation based on biological loading by adjusting one or more pathogen reduction devices UV disinfection cycle time, adjusting delay time thresholds for UV activation of one or more pathogen reduction devices, and adjusting UV intensity for one or more pathogen reduction devices.

11. The pathogen reduction control system of claim 1 wherein the sensor information includes HVAC activity information, and wherein the coordinating controller is configured to transmit override instructions responsive to HVAC activity.

12. The pathogen reduction control system of claim 1 wherein the coordinating controller is configured to access a spatial relationship of the plurality of pathogen reduction devices, and wherein the override instructions transmitted by the coordinating controller to the plurality of pathogen reduction devices are scaled based on the spatial relationship and a biological loading trigger causing the instructions to be transmitted.

13. The pathogen reduction control system of claim 1 wherein the sensor information includes pressure information, and wherein the coordinating controller is configured to estimate an expected change in biological loading level based on a pressure differential, and transmit override instructions to adjust at least one of intensity of a UV lamp, cycle time, and delay time before activating UV lamp after sensing movement.

14. The pathogen reduction control system of claim 1 wherein the coordinating controller is configured to coordinate the plurality of pathogen reduction devices based on HVAC operation to reduce HVAC ambient sound levels.

15. A dynamic treatment system for a building, the dynamic treatment system comprising:
a plurality of zone controllers, each associated with one of a plurality of different respective zones of the building, and each configured to:
receive sensor information from one or more sensors associated with the respective zone of the building, the sensor information including one or more of occupancy information, temperature information, pressure information, air quality information, or humidity information;
identify a biological loading level of the respective zone of the building based on the received sensor information; and
transmit override instructions based on the identified biological loading level of the respective zone of the building; and
a plurality of air treatment devices disposed throughout the building in the plurality of different zones of the building, each air treatment device including a UV source, a fan, a communication interface, a controller, and memory, each air treatment device being configured to at least one of:
reduce pathogens by operating according to baseline instructions stored locally in memory and without influence from the plurality of zone controllers, wherein the baseline instructions control operation of the air treatment device based on one or more associated sensors providing one or more of timing information, airflow information, infrared information, motion information, accelerometer information, and temperature information, and
reduce pathogens by operating based on override instructions received from one of the plurality of zone controllers;
whereby the plurality of zone controllers and the plurality of air treatment devices cooperate to provide coordinated pathogen reduction within different zones of the building.

16. The dynamic treatment system of claim 15 including an occupancy sensor associated with each of the plurality of air treatment devices configured to detect occupancy.

17. The dynamic treatment system of claim 16 wherein each occupancy sensor is configured to output an average baseline of activity.

18. The dynamic treatment system of claim 15 including a pressure sensor configured to detect a pressure level.

19. The dynamic treatment system of claim 15 including a multi-level particulate sensor configured to measure microdroplets.

20. The dynamic treatment system of claim 19 wherein the multi-level particulate sensor is configured to measure microdroplets at different sizes, volume per cubic foot adjusting one or more pathogen reduction devices UV disinfection cycle time, adjusting delay time thresholds for UV activation of one or more pathogen reduction devices, and adjusting UV intensity for one or more pathogen reduction devices.

21. The pathogen reduction control system of claim 15 wherein the plurality of local controllers are each configured to identify a biological loading level of the respective zone of the building based on an increase in biological load within a particular zone of the building and wherein the plurality of local controllers are each configured to transmit override instructions in response to adjust the biological loading level of the respective zone.

\

UNITED STATES PATENT AND TRADEMARK OFFICE
CERTIFICATE OF CORRECTION

| | |
|---|---|
| PATENT NO. | : 12,053,559 B2 |
| APPLICATION NO. | : 17/364189 |
| DATED | : August 6, 2024 |
| INVENTOR(S) | : David W Baarman et al. |

It is certified that error appears in the above-identified patent and that said Letters Patent is hereby corrected as shown below:

In the Claims

Column 39, Claim 7, Line 22:
"including wherein the plurality of pathogen reduction"

Should be:
– wherein the plurality of pathogen reduction –

Column 40, Claim 20, Lines 55-59:
"The dynamic treatment system of claim 19 wherein the multi-level particulate sensor is configured to measure microdroplets at different sizes, volume per cubic foot adjusting one or more pathogen reduction devices UV disinfection cycle time, adjusting delay time thresholds for UV activation of one or more pathogen reduction devices, and adjusting UV intensity for one or more pathogen reduction devices."

Should be:
– The dynamic treatment system of claim 19 wherein the multi-level particulate sensor is configured to measure microdroplets at different sizes, volume per cubic foot. –

Signed and Sealed this
Fourteenth Day of January, 2025

Derrick Brent
*Acting Director of the United States Patent and Trademark Office*